(12) United States Patent
Andersson et al.

(10) Patent No.: US 12,143,777 B2
(45) Date of Patent: Nov. 12, 2024

(54) ADVANCED BONE CONDUCTION IMPLANT

(71) Applicant: Cochlear Limited, Macquarie University (AU)

(72) Inventors: Marcus Andersson, Macquarie University (AU); Stefan Magnander, Macquarie University (AU); Goran Bjorn, Macquarie University (AU); Jerry Frimanson, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 309 days.

(21) Appl. No.: 17/280,289

(22) PCT Filed: Dec. 20, 2019

(86) PCT No.: PCT/IB2019/061215
§ 371 (c)(1),
(2) Date: Mar. 26, 2021

(87) PCT Pub. No.: WO2020/129021
PCT Pub. Date: Jun. 25, 2020

(65) Prior Publication Data
US 2022/0046368 A1    Feb. 10, 2022

Related U.S. Application Data

(60) Provisional application No. 62/784,081, filed on Dec. 21, 2018.

(51) Int. Cl.
*A61B 17/86*    (2006.01)
*A61B 17/16*    (2006.01)
*H04R 25/00*    (2006.01)

(52) U.S. Cl.
CPC ....... *H04R 25/606* (2013.01); *A61B 17/1695* (2013.01)

(58) Field of Classification Search
CPC .............. H04R 25/606; H04R 2460/13; H04R 1/1016; H04R 1/1091; H04R 9/025;
(Continued)

(56) References Cited

U.S. PATENT DOCUMENTS 7,466,833 B2 *  12/2008  Lee ..................... H04M 1/03
                                                    381/151
8,737,649 B2 *  5/2014   Parker ................ H04R 25/606
                                                    381/151
(Continued)

FOREIGN PATENT DOCUMENTS

JP        2010075394 A    4/2010

OTHER PUBLICATIONS

International Search Report & Written Opinion for PCT/IB2019/061215, mailed Apr. 16, 2020.

*Primary Examiner* — Gerald Gauthier
(74) *Attorney, Agent, or Firm* — Pilloff Passino & Cosenza LLP; Martin J. Cosenza

(57) ABSTRACT

An apparatus, including an implantable portion of a transcutaneous bone conduction device and a pedestal attached to the implantable portion, the pedestal configured to be implanted into a skull bone of a recipient. In an exemplary embodiment, the apparatus is an implantable portion of a transcutaneous bone conduction device that can be fully covered by skin of a recipient.

24 Claims, 33 Drawing Sheets

(58) Field of Classification Search
CPC ..... H04R 11/00; H04R 25/60; A61B 17/1695; A61B 17/86; A61B 17/8615; A61B 17/8635; A61N 1/36036; H04M 1/03
See application file for complete search history.

(56) References Cited

U.S. PATENT DOCUMENTS

| | | | | |
|---|---|---|---|---|
| 8,965,021 | B2* | 2/2015 | Adamson | H04R 25/606 |
| | | | | 381/151 |
| 9,137,614 | B2* | 9/2015 | Westerkull | H04R 25/606 |
| 9,545,522 | B2 | 1/2017 | Gibson et al. | |
| 9,731,128 | B2 | 8/2017 | Leigh et al. | |
| 10,003,898 | B1* | 6/2018 | Bjorn | H04R 25/606 |
| 10,750,298 | B2* | 8/2020 | Jinton | A61B 17/8615 |
| 2004/0028249 | A1* | 2/2004 | Asnes | H04R 9/025 |
| | | | | 381/151 |
| 2004/0057588 | A1* | 3/2004 | Asnes | H04R 25/606 |
| | | | | 381/151 |
| 2004/0210103 | A1* | 10/2004 | Westerkull | H04R 25/606 |
| | | | | 600/25 |
| 2006/0098829 | A1* | 5/2006 | Kobayashi | H04R 1/1091 |
| | | | | 381/151 |
| 2006/0126874 | A1* | 6/2006 | Westerkull | H04R 25/606 |
| | | | | 381/151 |
| 2009/0023109 | A1* | 1/2009 | Jinton | A61B 17/8615 |
| | | | | 433/174 |
| 2009/0240099 | A1 | 9/2009 | Conn | |
| 2010/0209873 | A1* | 8/2010 | Asnes | H04R 25/606 |
| | | | | 433/174 |
| 2011/0135120 | A1* | 6/2011 | Larsen | H04R 1/1016 |
| | | | | 381/151 |
| 2011/0243356 | A1 | 10/2011 | Koike et al. | |
| 2012/0078035 | A1* | 3/2012 | Andersson | H04R 25/606 |
| | | | | 600/25 |
| 2012/0172658 | A1 | 7/2012 | Bjorn et al. | |
| 2012/0302822 | A1* | 11/2012 | Van Himbeeck | H04R 1/1091 |
| | | | | 381/151 |
| 2012/0302823 | A1* | 11/2012 | Andersson | H04R 11/00 |
| | | | | 381/326 |
| 2013/0090518 | A1* | 4/2013 | Bjorn | H04R 25/606 |
| | | | | 600/25 |
| 2013/0114834 | A1* | 5/2013 | Bern | H04R 25/606 |
| | | | | 381/151 |
| 2013/0281764 | A1* | 10/2013 | Bjorn | H04R 25/606 |
| | | | | 600/25 |
| 2014/0275731 | A1* | 9/2014 | Andersson | H04R 25/606 |
| | | | | 600/25 |
| 2015/0038775 | A1* | 2/2015 | Ruppersberg | H04R 25/606 |
| | | | | 523/105 |
| 2015/0094522 | A1* | 4/2015 | Mauger | H04R 25/606 |
| | | | | 600/25 |
| 2015/0215696 | A1* | 7/2015 | Bjorn | H04R 25/606 |
| | | | | 600/25 |
| 2015/0312687 | A1* | 10/2015 | Andersson | H04R 25/606 |
| | | | | 600/25 |
| 2016/0058454 | A1* | 3/2016 | Andersson | A61B 17/8635 |
| | | | | 600/25 |
| 2016/0234613 | A1* | 8/2016 | Westerkull | H04R 25/60 |
| 2016/0249143 | A1* | 8/2016 | Andersson | H04R 25/60 |
| 2018/0036537 | A1* | 2/2018 | Van den Heuvel | A61N 1/36036 |
| 2018/0220245 | A1 | 8/2018 | Jinton et al. | |
| 2022/0046368 | A1* | 2/2022 | Andersson | H04R 25/606 |
| 2022/0370107 | A1* | 11/2022 | Millg?rd | A61B 17/86 |

* cited by examiner

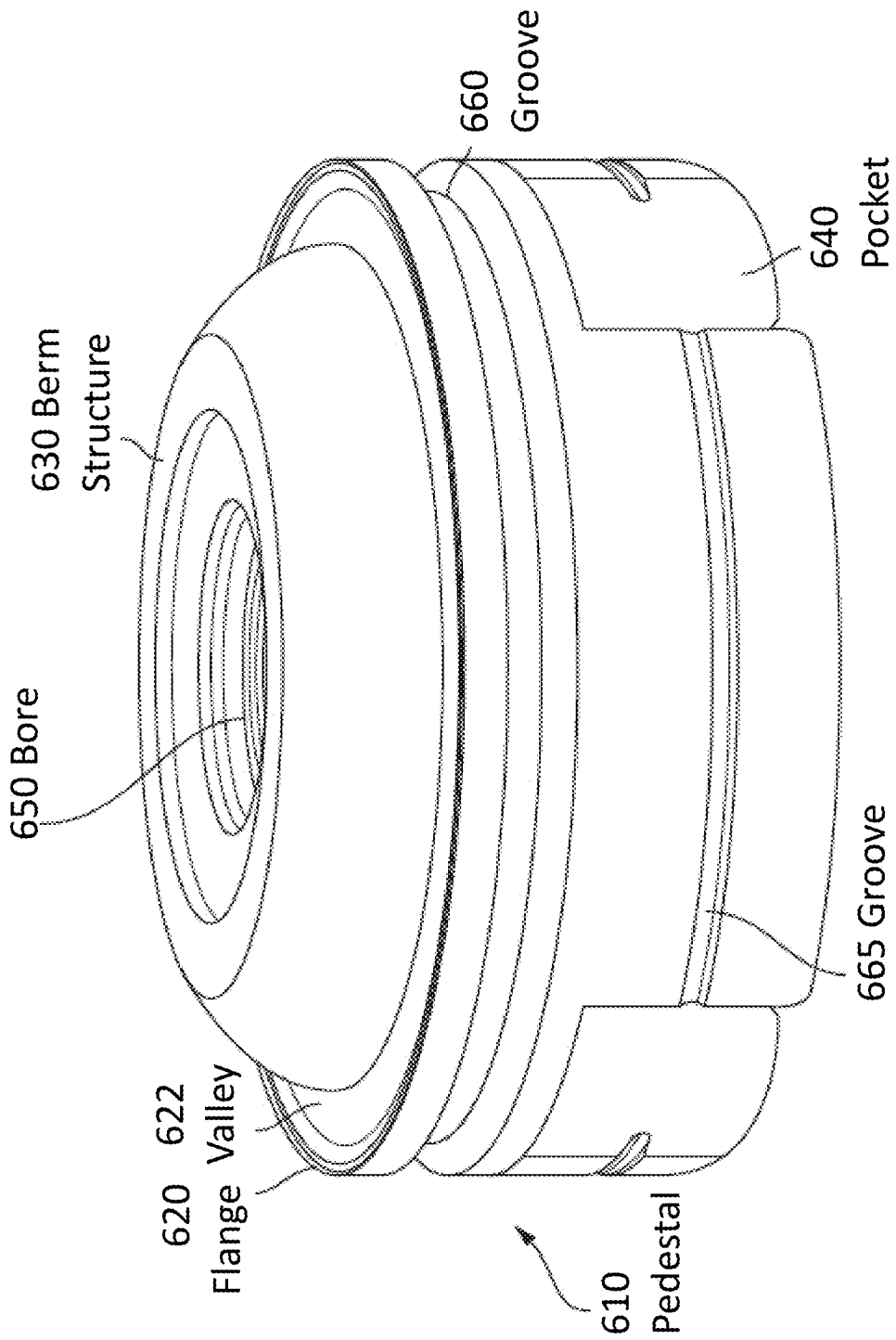

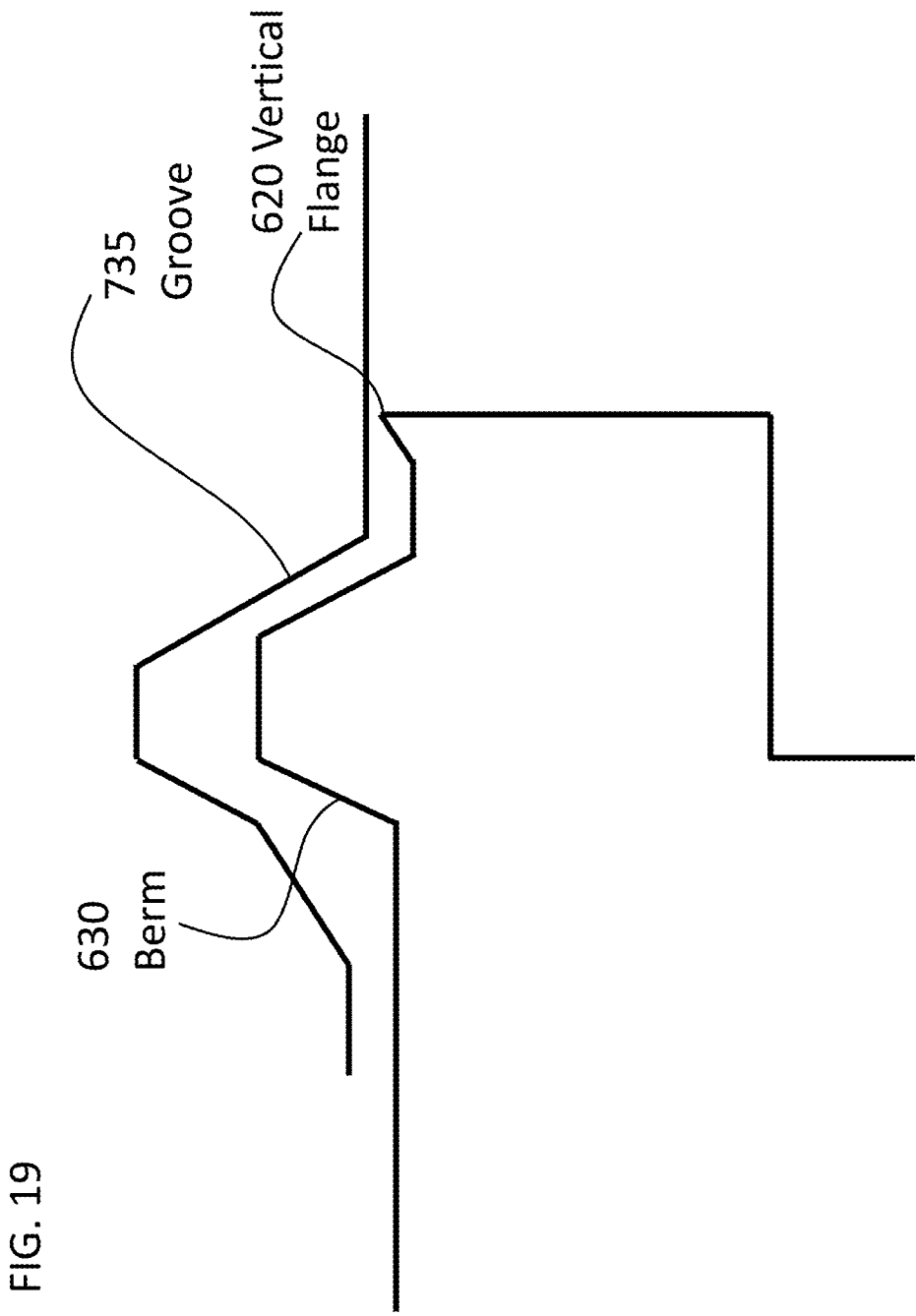

ADVANCED BONE CONDUCTION IMPLANT

CROSS-REFERENCE TO RELATED APPLICATIONS

This application claims priority to U.S. Provisional Application No. 62/784,081, entitled ADVANCED BONE CONDUCTION IMPLANT, filed on Dec. 21, 2018, naming Marcus ANDERSSON of Molnlycke, Sweden as an inventor, the entire contents of that application being incorporated herein by reference in its entirety.

BACKGROUND

Field of the Invention

Some embodiments relate generally to prostheses and, more particularly, to a prosthesis having a bone fixture.

Related Art

For persons who cannot benefit from traditional acoustic hearing aids, there are other types of commercially available hearing prostheses such as, for example, bone conduction hearing prostheses (commonly referred to as "bone conduction devices"). Bone conduction devices mechanically transmit sound information to a recipient's cochlea by transferring vibrations to a person's skull. This enables the hearing prosthesis to be effective regardless of whether there is disease or damage in the middle ear.

Traditionally, bone conduction devices transfer vibrations from an external vibrator to the skull through a bone conduction implant that penetrates the skin and is physically attached to both the vibrator and the skull. Typically, the external vibrator is connected to the percutaneous bone conduction implant located behind the outer ear facilitating the efficient transfer of sound via the skull to the cochlea. The bone conduction implant connecting the vibrator to the skull generally comprises two components: a bone attachment piece (e.g., bone fixture/fixture) that is attached or implanted directly to the skull, and a skin penetrating piece attached to the bone attachment piece, commonly referred to as an abutment.

SUMMARY

In one embodiment, there is an apparatus, comprising an implantable portion of a transcutaneous bone conduction device and a pedestal attached to the implantable portion, the pedestal configured to be implanted into a skull bone of a recipient.

In another embodiment, there is a method, comprising obtaining an implantable portion of a transcutaneous bone conduction device and attaching a pedestal to the implantable portion temporally proximate to implanting such into a recipient, the pedestal configured to be implanted into a skull bone of a recipient. In another embodiment, there is an apparatus, comprising an osseointegrating lateral stability device configured for removable attachment to an implantable prosthetic component, the device having non-threaded bone interfacing surfaces extending for at least about half a longitudinal distance of the device.

BRIEF DESCRIPTION OF THE DRAWINGS

Embodiments of the present invention are described herein with reference to the attached drawing sheets in which:

FIG. 6A and FIG. 6B depict isometric views of an exemplary pedestal according to an exemplary embodiment;

FIGS. 19 and 20 depict an exemplary action of attaching the pedestal to the implantable portion.

DETAILED DESCRIPTION

Figure 1:
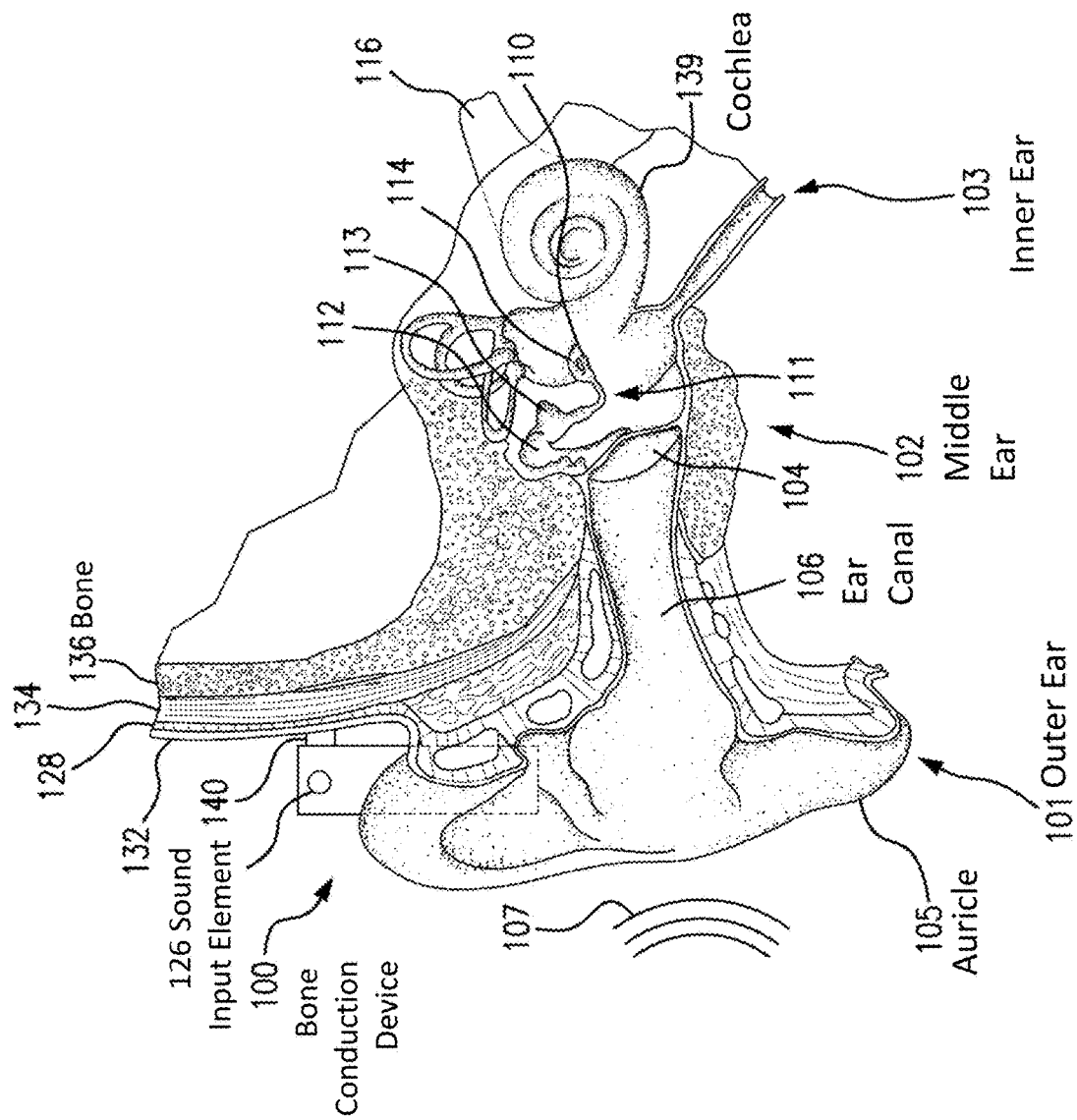
FIG. 1 is a perspective view of a percutaneous bone conduction device in which embodiments of the present invention may be implemented.

FIG. 1 is a perspective view of a bone conduction device 100 in which embodiments of the present invention can be implemented. As shown, the recipient has an outer ear 101, a middle ear 102 and an inner ear 103. Elements of outer ear 101, middle ear 102 and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 210 through three bones of middle ear 102, collectively referred to as the ossicles 111 and comprising the malleus 112, the incus 113 and the stapes 114. The ossicles 111 of middle ear 102 serve to filter and amplify acoustic wave 107, causing oval window 210 to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 is positioned behind outer ear 101 of the recipient and comprises a sound input element 126 to receive sound signals. Sound input element can comprise, for example, a microphone, telecoil, etc. In an exemplary embodiment, sound input element 126 can be located, for example, on or in bone conduction device 100, or on a cable extending from bone conduction device 100.

In an exemplary embodiment, bone conduction device 100 comprises an operationally removable component and a bone conduction implant. The operationally removable component is operationally releasably coupled to the bone conduction implant. By operationally releasably coupled, it is meant that it is releasable in such a manner that the recipient can relatively easily attach and remove the operationally removable component during normal use of the bone conduction device 100. Such releasable coupling is accomplished via a coupling apparatus of the operationally removable component and a corresponding mating apparatus of the bone conduction implant, as will be detailed below. This as contrasted with how the bone conduction implant is attached to the skull, as will also be detailed below. The operationally removable component includes a sound processor (not shown), a vibrating electromagnetic actuator and/or a vibrating piezoelectric actuator and/or other type of actuator (not shown—which are sometimes referred to herein as a vibrator, corresponding to a genus of which these are species of) and/or various other operational components, such as sound input device 126. In this regard, the operationally removable component is sometimes referred to herein as a vibrator unit. More particularly, sound input device 126 (e.g., a microphone) converts received sound signals into electrical signals. These electrical signals are processed by the sound processor. The sound processor generates control signals which cause the actuator to vibrate. In other words, the actuator converts the electrical signals into mechanical motion to impart vibrations to the recipient's skull. It is noted that in some embodiments, the operationally removable component is a vibration sensor. In this regard, the operationally removable component can be a transducer, which is a genus that includes at least the species vibration sensor and vibrator.

As illustrated, the operationally removable component of the bone conduction device 100 further includes a coupling apparatus 140 configured to operationally removably attach the operationally removable component to a bone conduction implant (also referred to as an anchor system and/or a fixation system) which is implanted in the recipient. In the embodiment of FIG. 1, coupling apparatus 140 is coupled to the bone conduction implant (not shown) implanted in the recipient in a manner that is further detailed below with respect to exemplary embodiments of the bone conduction implant. Briefly, now with reference to FIG. 2A, an exemplary bone conduction implant 201 can include a percutaneous abutment attached to a bone fixture via a screw, the bone fixture being fixed to the recipient's skull bone 136. The abutment extends from the bone fixture which is screwed into bone 136, through muscle 134, fat 128 and skin 132 so that the coupling apparatus can be attached thereto. Such a percutaneous abutment provides an attachment location for the coupling apparatus that facilitates efficient transmission of mechanical force.

Figure 2:
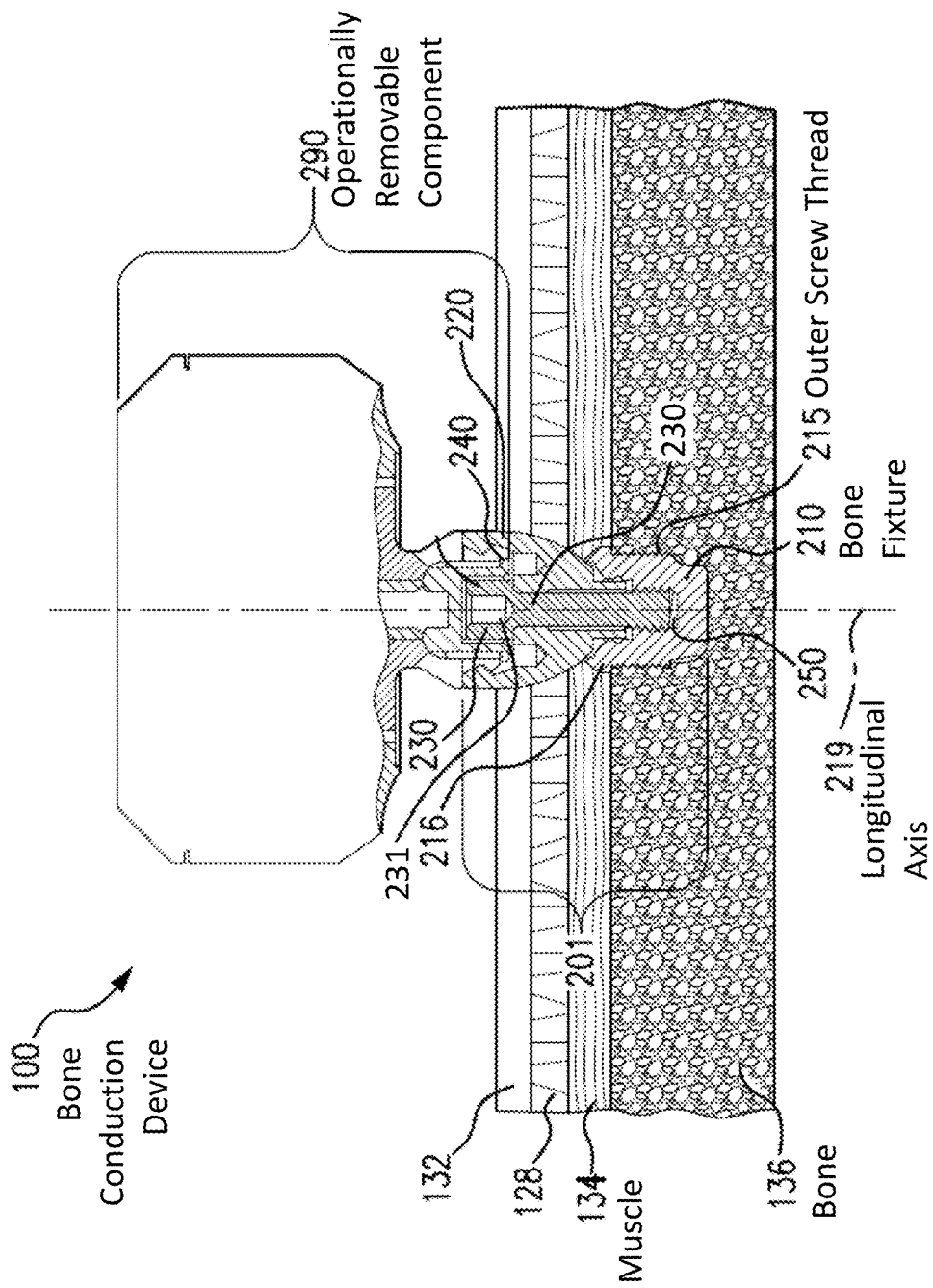
FIG. 2 depicts a more detailed view of the bone conduction device of FIG. 1.

FIG. 2 depicts additional details of the bone conduction device 100. More particularly, the bone conduction device 100 is shown as including operationally removable component 290 vibrationally connected to and removably coupled to an exemplary bone conduction implant 201 via coupling apparatus 140 (corresponding to coupling apparatus 240) thereof. More particularly, operationally removable component 290 includes a vibrator (not shown) that is in vibrational communication to coupling apparatus 240 such that vibrations generated by the vibrator in response to a sound captured by sound capture device 126 are transmitted to coupling apparatus 240 and then to bone conduction implant 201 in a manner that at evokes hearing percept.

Bone conduction implant 201 includes a bone fixture 210 configured to screw into the skull bone 136, a skin-penetrating abutment 220 and an abutment screw 230 that is in the form of an elongate coupling shaft. As may be seen, the abutment screw 230 connects and holds the abutment 220 to the fixture 210, thereby rigidly attaching abutment 220 to bone fixture 210. The rigid attachment is such that the abutment is vibrationally connected to the fixture 210 such that at least some of the vibrational energy transmitted to the abutment is transmitted to the fixture in a sufficient manner to effectively evoke a hearing percept. The abutment screw can have a recess 231 that is a hexagonal recess or the like to receive a hex head wrench for torque application purposes. The bone fixture can have a threaded bore 250 to receive an abutment screw 230.

Some exemplary features of the bone fixture 210 will now be described.

Bone fixture 210 (hereinafter sometimes referred to as fixture 210) can be made of any material that has a known ability to integrate into surrounding bone tissue (i.e., it is made of a material that exhibits acceptable osseointegration characteristics). In one embodiment, fixture 210 is formed from a single piece of material (it is a monolithic component) and has a main body. In an embodiment, the fixture 210 is made of titanium. The main body of bone fixture 210 includes outer screw thread 215 forming a male screw which is configured to be installed into the skull 136. Fixture 210 also comprises a flange 216 configured to function as a stop when fixture 210 is installed into the skull. Owing to the bottom surface of the flange (the part that contacts the top surface of the bone), flange 216 prevents the bone fixture 210 in general, and, in particular, screw threads 215, from potentially completely penetrating through the skull. Fixture 210 can further comprise a tool-engaging socket having an internal grip section for easy lifting and handling of fixture 210, as will be described in further detail below. An exemplary tool-engaging socket is described and illustrated in U.S. Provisional Application No. 60/951,163, entitled "Bone Anchor Fixture for a Medical Prosthesis," filed Jul. 20, 2007, by Applicants Lars Jinton, Erik Holgersson and Peter Elmberg which, in some embodiments, can be used exactly as detailed therein and/or in a modified form, to install and manipulate the bone fixture 210.

The body of fixture 210 can have a length sufficient to securely anchor the fixture 210 to the skull without penetrating entirely through the skull bone. The length of the body can therefore depend on the thickness of the skull at the implantation site. Some exemplary lengths are detailed below.

The distal region of fixture 210 can also be fitted with self-tapping cutting edges (e.g., three edges) formed into the exterior surface of the fixture 210. Further details of the self-tapping features are described in International Patent Application Publication WO 02/09622, and can be used with some embodiments of bone fixtures exactly as detailed therein and/or in a modified form, to configure the fixtures detailed herein to be installed into a skull.

As illustrated in FIG. 2, flange 216 has a substantially planar bottom surface for resting against the outer bone surface, when bone fixture 210 has been screwed down into the skull. Flange 216 can have a diameter which exceeds the peak diameter (maximum diameter) of the screw threads 215 (the screw threads 215 of the fixture 210 can have a maximum diameter of about 3.5 to about 5.0 mm). In one embodiment, the diameter of the flange 216 exceeds the peak diameter of the screw threads 215 by approximately 10-20%. Although flange 216 is illustrated in FIG. 2 as being circular, flange 216 can be configured in a variety of shapes so long as flange 216 has at least one of a diameter or width that is greater than the peak diameter of the screw threads 215. Also, the size of flange 216 can vary depending on the particular application for which the bone conduction implant 201 is intended.

In an exemplary embodiment, the flange 216 can be in the form of a protruding or recessed hex or other multi-lobs geometry instead of being circular. That is, flange 216 can have a hexagonal cross-section that lies on a plane normal to the longitudinal axis 219 of the bone fixture 220/bone conduction implant 201 such that a female hex-head socket wrench can be used to apply torque to the bone fixture 210. However, in the embodiment illustrated in FIG. 2, the flange 216 has a smooth, upper end that has a circular cross-section that lies on the aforementioned plane, and thus does not have a protruding hex. The smooth upper end of the flange 216 and the absence of any sharp corners provides for improved soft tissue adaptation. As mentioned above, flange 216 also comprises a cylindrical part which, together with the flared upper part, provides sufficient height in the longitudinal direction for connection with the abutment 220.

It is noted that the bone fixture depicted in FIG. 2 and the following FIGs. are exemplary. Any bone fixture and/or pedestal of any type, size/having any geometry can be used in some embodiments providing that the bone fixture permits embodiments as detailed herein and variations thereof to be practiced.

Figure 3:
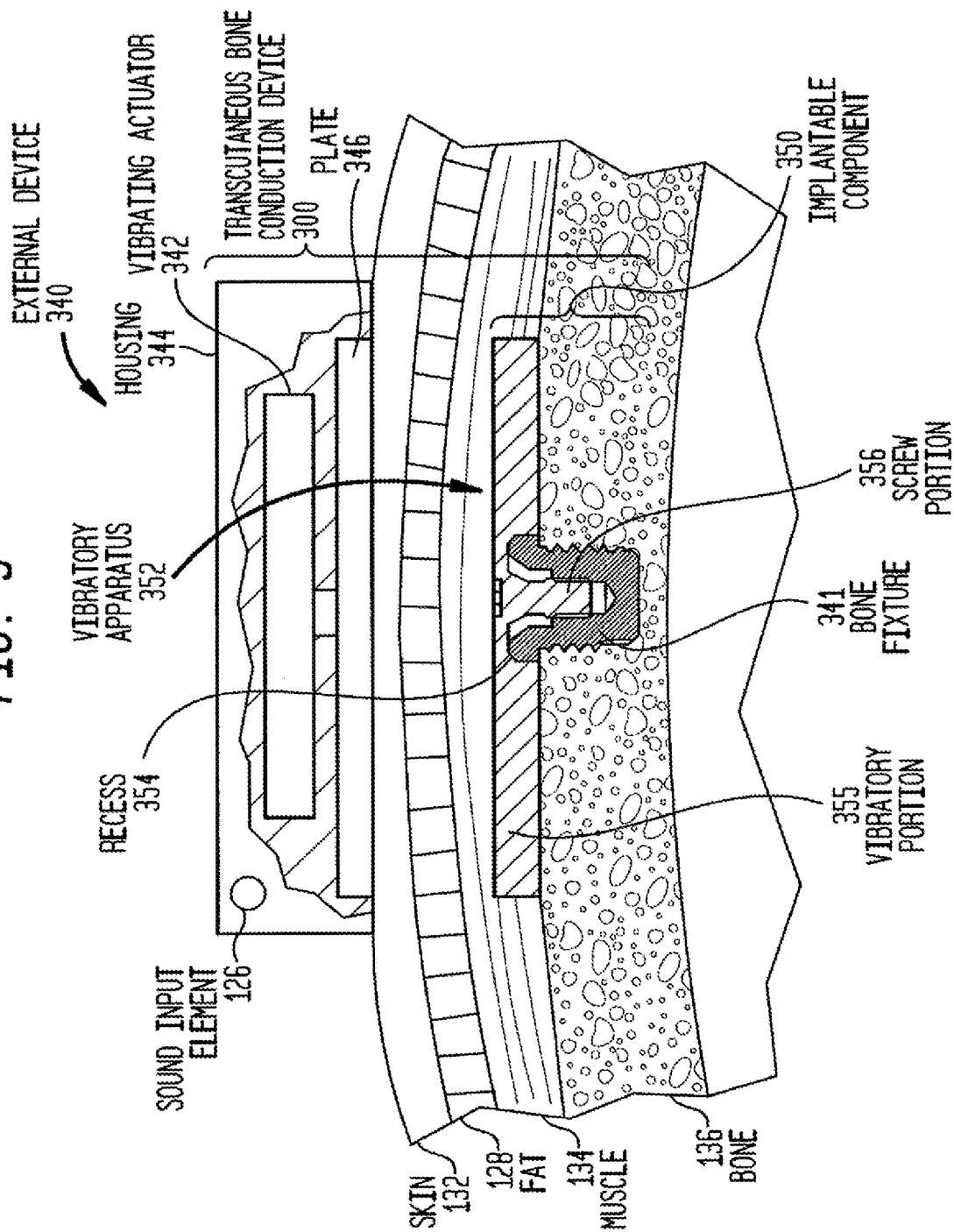
FIG. 3 depicts an exemplary passive transcutaneous bone conduction device.

FIG. 3 depicts an exemplary embodiment of a transcutaneous bone conduction device 300 according to an embodiment that includes an external device 340 (corresponding to, for example, element 140B of FIG. 1B) and an implantable component 350 (corresponding to, for example, element 150 of FIG. 1B). The transcutaneous bone conduction device 300 of FIG. 3 is a passive transcutaneous bone conduction device in that a vibrating electromagnetic actuator 342 is located in the external device 340. Vibrating electromagnetic actuator 342 is located in housing 344 of the external component, and is coupled to plate 346. Plate 346 may be in the form of a permanent magnet and/or in another form that generates and/or is reactive to a magnetic field, or otherwise permits the establishment of magnetic attraction between the external device 340 and the implantable component 350 sufficient to hold the external device 340 against the skin of the recipient.

In an exemplary embodiment, the vibrating electromagnetic actuator 342 is a device that converts electrical signals into vibration. In operation, sound input element 126 converts sound into electrical signals. Specifically, the transcutaneous bone conduction device 300 provides these electrical signals to vibrating actuator 342, or to a sound processor (not shown) that processes the electrical signals, and then provides those processed signals to vibrating electromagnetic actuator 342. The vibrating electromagnetic actuator 342 converts the electrical signals (processed or unprocessed) into vibrations. Because vibrating electromagnetic actuator 342 is mechanically coupled to plate 346, the vibrations are transferred from the vibrating actuator 342 to plate 346. Implanted plate assembly 352 is part of the implantable component 350, and is made of a ferromagnetic material that may be in the form of a permanent magnet, that generates and/or is reactive to a magnetic field, or otherwise permits the establishment of a magnetic attraction between the external device 340 and the implantable component 350 sufficient to hold the external device 340 against the skin of the recipient. Accordingly, vibrations produced by the vibrating electromagnetic actuator 342 of the external device 340 are transferred from plate 346 across the skin to plate 355 of plate assembly 352. This can be accomplished as a result of mechanical conduction of the vibrations through the skin, resulting from the external device 340 being in direct contact with the skin and/or from the magnetic field between the two plates. These vibrations are transferred without penetrating the skin with a solid object such as an abutment as detailed herein with respect to a percutaneous bone conduction device.

As may be seen, the implanted plate assembly 352 is substantially rigidly attached to a bone fixture 341 in this embodiment. Plate screw 356 is used to secure plate assembly 352 to bone fixture 341. The portions of plate screw 356 that interface with the bone fixture 341 substantially correspond to an abutment screw discussed in some additional detail below, thus permitting plate screw 356 to readily fit into an existing bone fixture used in a percutaneous bone conduction device. In an exemplary embodiment, plate screw 356 is configured so that the same tools and procedures that are used to install and/or remove an abutment screw (described below) from bone fixture 341 can be used to install and/or remove plate screw 356 from the bone fixture 341 (and thus the plate assembly 352).

Figure 4:
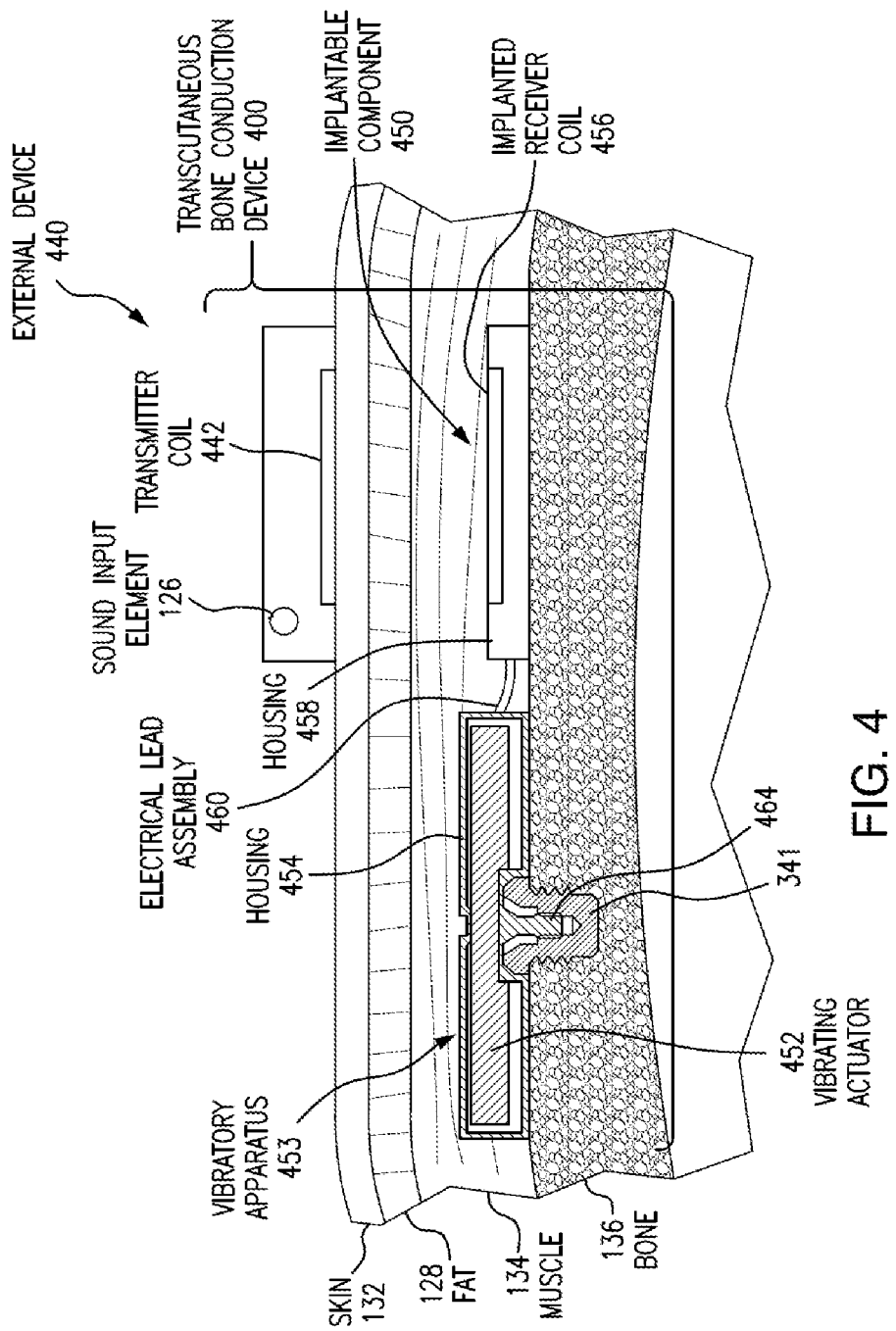
FIG. 4 depicts an exemplary active transcutaneous bone conduction device.

FIG. 4 depicts an exemplary embodiment of a transcutaneous bone conduction device 400 according to another embodiment that includes an external device 440 (corresponding to, for example, element 140B of FIG. 1B) and an implantable component 450 (corresponding to, for example, element 150 of FIG. 1B). The transcutaneous bone conduction device 400 of FIG. 4 is an active transcutaneous bone conduction device in that the vibrating actuator 452 is located in the implantable component 450. Specifically, a vibratory element in the form of vibrating actuator 452 is located in housing 454 of the implantable component 450. In an exemplary embodiment, much like the vibrating actuator 342 described above with respect to transcutaneous bone conduction device 300, the vibrating actuator 452 is a device that converts electrical signals into vibration.

External component 440 includes a sound input element 126 that converts sound into electrical signals. Specifically, the transcutaneous bone conduction device 400 provides these electrical signals to vibrating electromagnetic actuator 452, or to a sound processor (not shown) that processes the electrical signals, and then provides those processed signals to the implantable component 450 through the skin of the recipient via a magnetic inductance link. In this regard, a transmitter coil 442 of the external component 440 transmits these signals to implanted receiver coil 456 located in housing 458 of the implantable component 450. Components (not shown) in the housing 458, such as, for example, a signal generator or an implanted sound processor, then generate electrical signals to be delivered to vibrating actuator 452 via electrical lead assembly 460. The vibrating electromagnetic actuator 452 converts the electrical signals into vibrations.

The vibrating electromagnetic actuator 452 is mechanically coupled to the housing 454. Housing 454 and vibrating actuator 452 collectively form a vibrating element 453. The housing 454 is substantially rigidly attached to bone fixture 341.

Some exemplary bone fixtures that correspond to bone fixture 210 will now be described.

Figure 5:
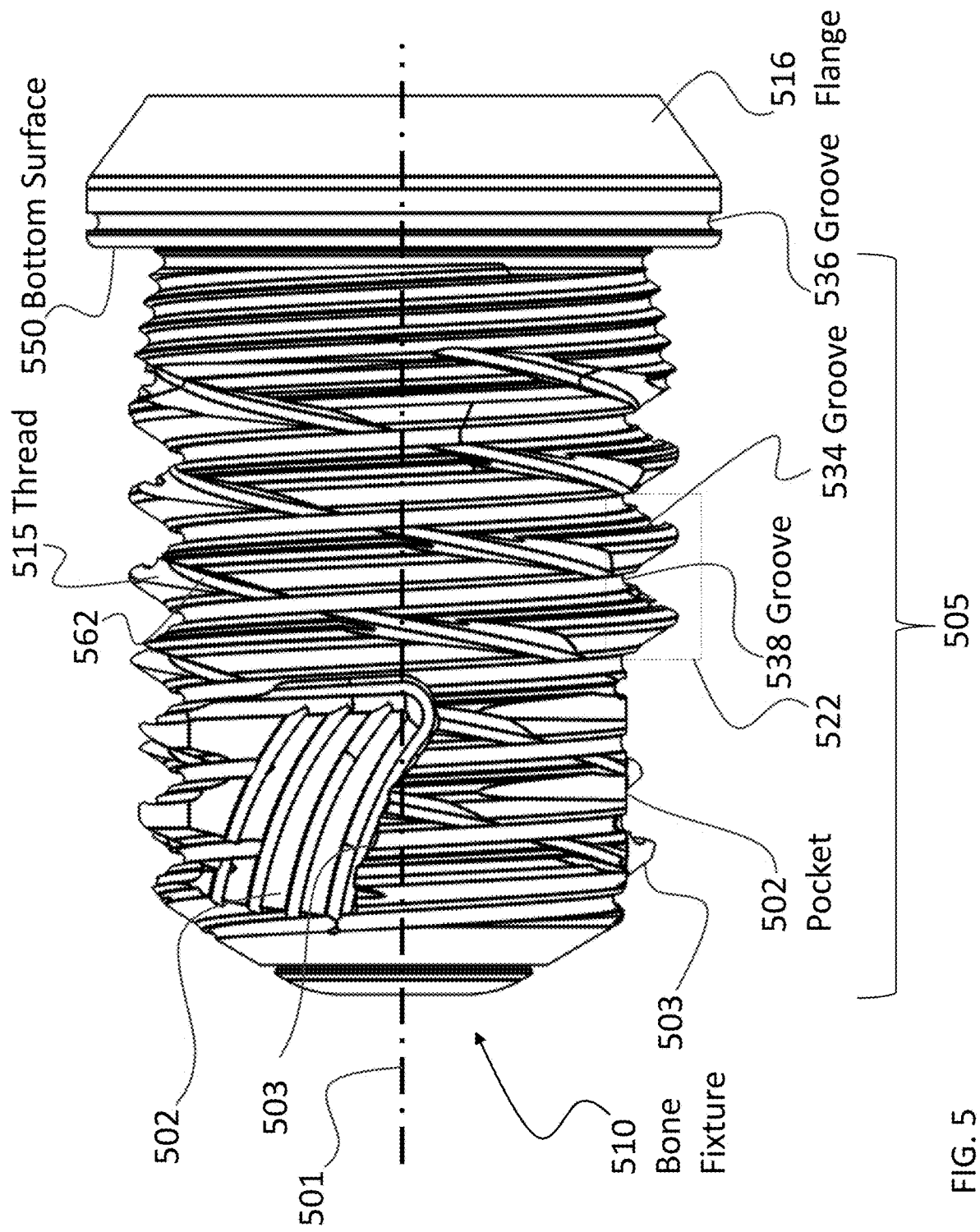
FIG. 5 depicts a side view of an exemplary bone screw.

FIG. 5 depict an exemplary embodiment of a bone fixture 510. In an exemplary embodiment, bone fixture 510 corresponds to bone fixture 210 of FIG. 2. Bone fixture 510 includes a screw thread 515 configured to screw into a skull, corresponding to thread 215 of FIG. 2. In an exemplary embodiment, the pitch of the screw thread 515 is between about 0.2 to about 1.00 mm or any value or range of values therebetween in about 0.01 mm increments (e.g., about 0.3 to about 0.8 mm). In an exemplary embodiment, the depth of the thread is between about 0.1 to about 1.25 mm or any value or range of values therebetween in about zero 0.1 mm increments (e.g., about 0.25 to about 0.8 mm).

In the embodiment of FIG. 5, a portion of the section of the screw thread that extends at least a portion of the way along the helix of the thread is non-uniform. By "section," it is meant the thread from tip to root.

In an exemplary embodiment, bone fixture 510 has a section 522 having such non-uniformity. As can be seen, the thread angle of the section is asymmetrical.

It is noted that in an alternate embodiment, the faces of the thread can be compound faces. That is, for example, one face of the thread may have a first surface that extends at a first angle from the centerline 523, and a second surface that extends at a second angle from the centerline 523 different from the first angle. In some instances, both faces of the thread may have such compound surfaces. Accordingly, in some embodiments, the aforementioned angles are measured from a location on the faces that corresponds to the same distance from the longitudinal axis 301 of the bone fixture 510/measured on a plane that is normal to the direction of centerline 523.

As can be seen in FIG. 5, the thread sections have grooves on the flanks thereof. More particularly, FIG. 5 depicts a portion 532 of the bone fixture 510 encompassing two sections of thread. As can be seen, the proximally facing flanks of the thread (i.e., the flanks of the thread that face the flange 516, or more particularly, face the bottom surface 550 of the flange 516 of the bone fixture 510, and thus face towards the proximal end of the bone fixture) have grooves 534 therein. It is noted that in alternative embodiment, the distally facing flanks of the threads (i.e., the flanks of the thread that face the end of the bone fixture 510/face away from the end that has the flange 516) have grooves therein. It is noted that in yet another alternative embodiment, both the proximally facing flanks and the distally facing flanks of the threads have grooves, where the grooves can be the same as each other and/or different from each other. In an exemplary embodiment, the depth of the 534 is in the range of about 50 to about 200 μm, and the width of the grooves 534 is in a range of about 70 to about 250 μm.

It is noted that in an exemplary embodiment, the depth of the groove is between about one-fourth and one-seventh the non-truncated height of the thread (distance from an extrapolated root to the extrapolated tip (i.e., the locations where the faces would converge if not for the rounding on the crest and the "sharp corner" relief at the root/base)).

It is noted that across-section of the grooves 534 can be substantially hemispherical with the "equator" aligned/flush with the top face of the thread. That said, other configurations can be utilized. By way of example only and not by way of limitation, if a hemispherical cross-section is to be utilized, the depth of the groove can be different from that which would result in the "equator" of the hemisphere being aligned/flush with the top face of the thread. (It is noted that the discussions herein with respect to the "shape" of the grooves 534, the shape corresponds to the cross-section of the grooves as taken on a plane that extends through and is parallel to the longitudinal axis 501 of the bone fixture 510). For example, the hypothetical equator could be proud (above) the face, thus resulting in a groove that is less than a complete hemisphere (the curvature from one face to the other would result in a portion of a circle less than 180 degrees). It is noted that the radius of the curved portion can be constant (i.e., R1=R2). In an alternate embodiment, the curved portion can be a compounded curve (R1 does not equal to R2 and/or there can be other different radii, etc.). In an alternate embodiment, the groove can be semi-spherical in cross-section. In this regard, the "equator" of the sphere can be below the top face (the curvature from one face to the other would result in a portion of a circle greater than 180 degrees). Still further, in an exemplary embodiment, the cross-section of the groove(s) can correspond to a "U" shape, with a bottom radius, and straight sides.

Again with reference to FIG. 5, it is noted that in some embodiments, the flange 516 of the bone fixture 510 includes a groove 536. It is noted that in the embodiments where the flange 516 includes groove(s), the grooves can correspond to any of the grooves detailed herein and/or variations thereof and/or any other shaped groove that can have utilitarian value and/or otherwise can enable the teachings detailed herein and/or variations thereof to be practiced.

Again with reference to FIG. 5, some embodiments include grooves 538 at the root (i.e., where the flanks of the thread converge, also referred to as base) of the thread. As can be seen, the root of the thread has a groove 538 therein. In an exemplary embodiment, the depth of the grooves 538 is in the range of about 50 to 200 μm, and the width of the grooves 538 is in a range of about 70 to 250 μm.

It is noted that in the embodiments where the root of the thread includes the groove, the groove can correspond to any of the grooves detailed herein and/or variations thereof and/or any other shaped groove that can have utilitarian value and/or otherwise can enable the teachings detailed herein and/or variations thereof to be practiced.

In at least some embodiments, the groove of the root runs with substantially all (including all) of the full sections of thread (again, a "full" thread section is discussed further below). In an exemplary embodiment, the grooves can run with less than substantially all of the full sections of the thread. In some embodiments, the groove runs a length that corresponds to a minority of the length of the full section of thread (i.e. the total helical length of the groove is less than half that of the total helical length of the full section of thread).

Also, the groove 538 can be present in multiple segments. That is, it can run with a portion of the thread, and then stop, and then begin again, and then stop, etc. It is noted that this is the case for the groove 338 and for any of the other grooves detailed herein (e.g., groove 5, etc.).

Figure 5A:
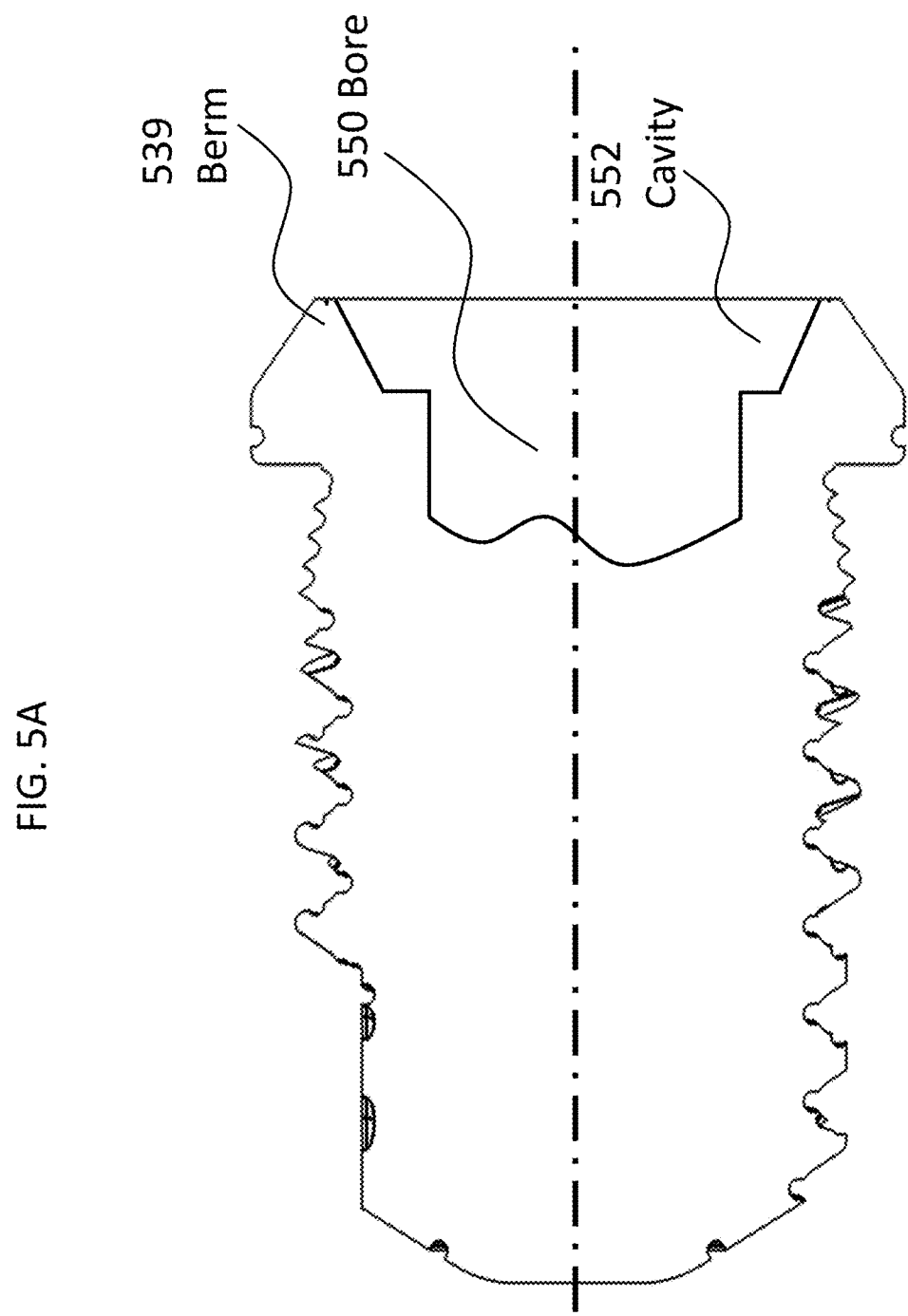
FIG. 5A depicts a cross-sectional view of the exemplary bone screw of FIG. 5.

FIG. 5A presents a partial cross-sectional view of the bone fixture of FIG. 5. Here, there is a bore 550 to receive the abutment screw. The inside of the bore is threaded, at least partially. The bore opens up into a cavity 552 that is established by wall/berm 539, which wall/berm extends about the longitudinal axis of the bone fixture.

As can be seen in the figures, the groove(s) run parallel to the thread direction. As will be discussed below, in some other embodiments, grooves can run in a different direction.

Any type of groove that can enable the teachings detailed herein and/or variations thereof to be practiced can be utilized in at least some embodiments.

As noted above, the exemplary embodiments of the bone fixture 510 of FIG. 5, includes a flat section 502. In an exemplary embodiment, the flat section 502 is a cutting pocket extending across two or more thread crests relative to the longitudinal axis 501 of the bone fixture 510 (the embodiment depicted in FIG. 5 has a cutting pocket extending across three thread crests). In some embodiments, there are one or more such cutting pockets. In an exemplary embodiment, there is a bone fixture that has three such cutting pockets arrayed symmetrically (which includes symmetrically) about the longitudinal axis 501 (i.e., at about 120-degree increments). In an exemplary embodiment, there is a bone fixture having one, two, three, four, five, six, seven, eight or more cutting pockets (in some embodiments, these are not cutting pockets, but instead simple pockets) or any value or range of values therebetween in integer increments. In some embodiments, these are arrayed symmetrically about the longitudinal axis 501. That said, in an alternate embodiment, the cutting pockets are not arrayed symmetrically/they are arrayed asymmetrically about the longitudinal axis 501. Further, while the embodiment of the pocket 502 depicted in FIG. 5 extends across three thread crests, in alternate embodiments, cutting pockets can extend across one, two, three, four, five, six or more thread crests or any value or range of values therebetween in integer increments. It is noted that in embodiments that utilize more cutting pockets than that of other embodiments, the cutting pockets of the former can have dimensions that are smaller relative to those of the latter, so as to, for example, provide sufficient space for the pockets. For example, the former can have cutting pockets that are shallower than the latter. By way of example only and not by way of limitation, such can have utility in embodiments where the cutting pockets are formed by flats; the shallower the cutting pockets, the less circumferential area that the cutting pockets take up relative to rotation about the longitudinal axis 501, Thus providing more room for additional pockets relative to that which would be the case in the absence of the shallower cutting pockets.

Note further, that in some embodiments, the cutting pockets are not uniform. That is, in some embodiments, the bone fixture has two or more cutting pockets, where one or more cutting pockets is different from one or more other cutting pockets.

In an exemplary embodiment, the pockets 502 provide for respective cutting edge lines 503, where the edge lines 503 is defined by the edges of the thread. In an exemplary embodiment, the cutting pockets 302 in general, and the edge lines 503 particular, provide a self-tapping functionality of the bone fixture 510.

With reference to FIG. 5, the cutting pocket 502, or more particularly, the cutting edge 503 of the cutting pocket 502, is a spiral cutting pocket. That is, instead of the cutting edge 503 extending in the longitudinal direction in a manner that is substantially parallel to the longitudinal axis 501, the cutting edge 503 spiral about the longitudinal axis 501. In the embodiment depicted in FIG. 5, the cutting edge 503 spirals in a direction counter to the direction of the thread 515. That said, in an alternate embodiment, the cutting edge 503 can spiral in a direction consistent with the direction of the thread 515.

With respect to the embodiment of FIG. 5, the pitch of the threads 5 are right-handed, while the pitch of the spiral cutting edge 503 is left-handed. In the embodiment of FIG. 5, the relative pitch of the threads 515 is smaller than that of the cutting edge 503. Continuing in terms of pitch, the cutting edges 503 can be considered as a thread about the longitudinal axis 501, where embodiments of the bone fixture that have two or three or four, etc., pockets 502 correspond to, respectively a bone fixture having a double, triple, or quintuple, etc., threaded body vis-à-vis the cutting edge.

Further, the pitch of the spiral cutting-edge 503 can be uniform relative to location along the longitudinal axis 3501, or can vary relative to the location along the longitudinal axis 501. Further, in an exemplary embodiment, one or more portions of the cutting edge 503 can be spiral, and one or more portions of the cutting-edge can extend parallel to the direction of the longitudinal axis 501. In an exemplary embodiment of the aforementioned exemplary embodiment, one or more portions of the cutting edge 503 that spiral can spiral in one direction (e.g., counter to the direction of the threads 515), and one or more portions of the cutting edge 503 that spiral can spiral in counter direction (e.g., consistent with the direction of the threads 515). Note further, in an exemplary embodiment of this exemplary embodiment, there may not be any portions of the cutting edge 503 that extend parallel to the direction the longitudinal axis 501. That is, in an exemplary embodiment, the cutting edge 503 spirals in one direction, and then spirals in a counter direction without extending in a direction parallel to the longitudinal axis 501. Note further that an exemplary embodiment includes any of the aforementioned embodiments, where the pitch of the spiral cutting edge 503 varies with position along the longitudinal axis 501 as detailed above.

Figure 6B:
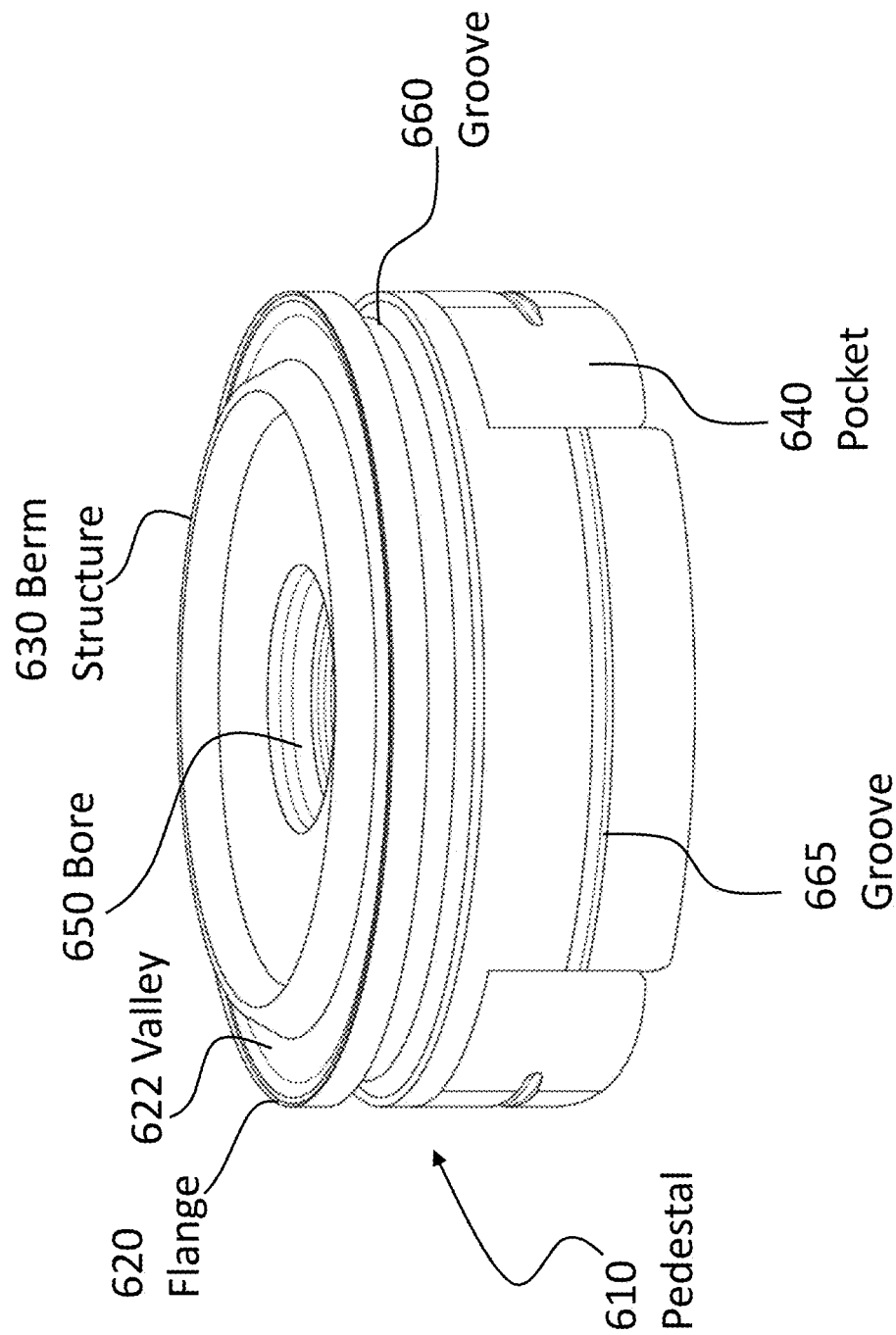

FIGS. 6A and 6B depict another type of bone implant, different from the embodiment of FIGS. 5 and 2. Here a pedestal structure 610 is presented, which is a substitute/alternative, to the bone fixture 510 presented above. That is, in an exemplary embodiment, the pedestal structure 610 of FIG. 6 is utilized to immobilize or otherwise maintain an implanted portion (e.g., the vibratory portion 355, the magnet of the arrangement of FIG. 3, the vibratory apparatus 453 of FIG. 4, etc.), at least in the lateral plane, of the implantable portion of a transcutaneous bone conduction device. In an exemplary embodiment, suturing or the like can be utilized over the implantable portion to prevent the device from popping out. Still further, in some other embodiments, small (relative to the pedestal) bone screws can be utilized to control the longitudinal movement of the implantable portion or otherwise provide additional retention in that dimension.

Figure 7:
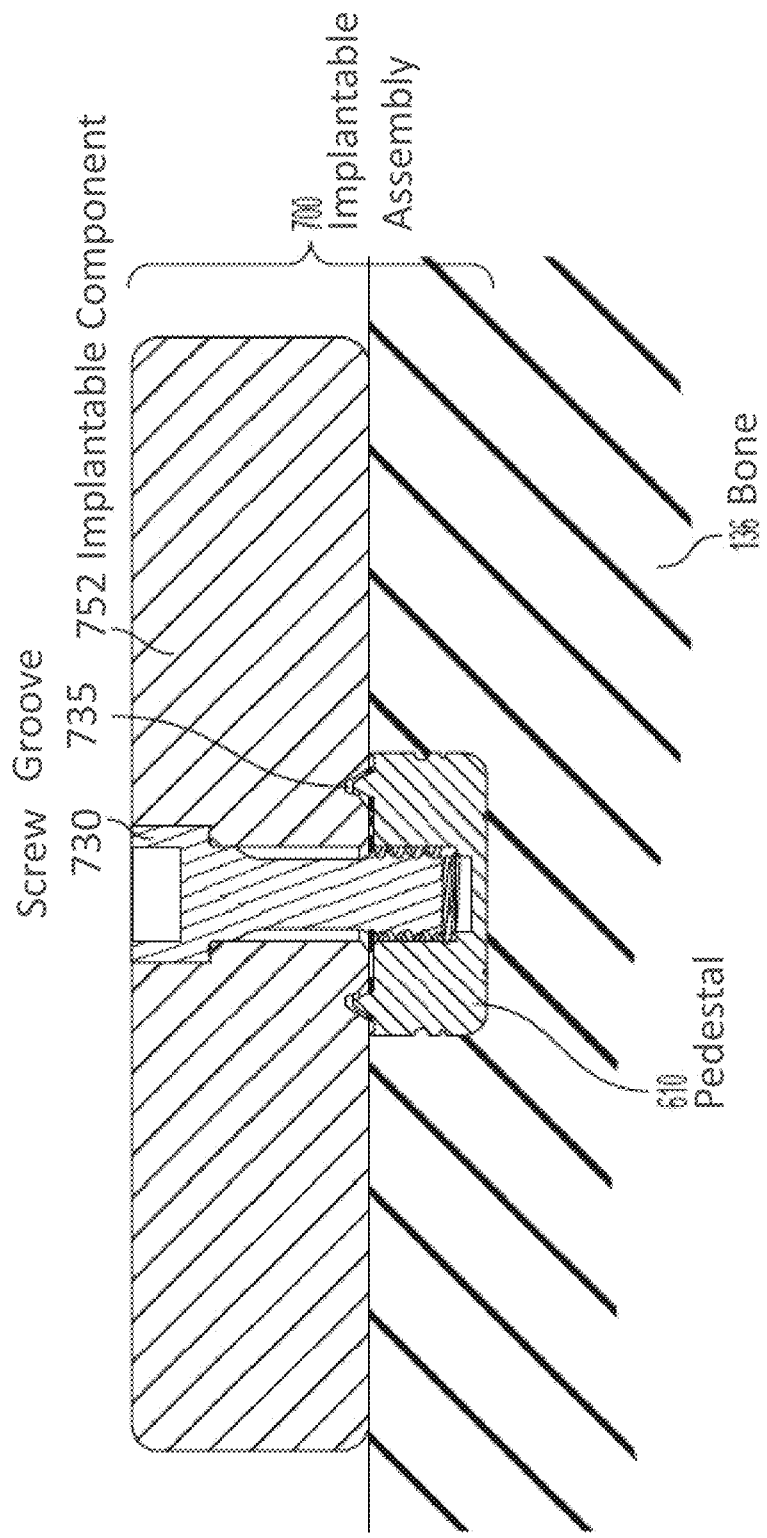
FIG. 7 depicts a cross-sectional quasi black box diagram of an exemplary implantable component according to an exemplary embodiment implanted into a recipient.

Briefly, the pedestal 610 includes a threaded bore 650 into which a fastening screw can be screwed therein to attach the implantable portion of a transcutaneous bone conduction device there too. FIG. 7 depicts an exemplary arrangement of an implantable assembly 700, which includes the implantable portion 752 of a transcutaneous bone conduction device attached to the pedestal 610 via screw 730. In this exemplary embodiment, the pedestal structure is releasably connected to the implantable portion, which releasable connection can be released via unscrewing the screw 750. Here, the pedestal 610 is implanted in bone 136 (more on this below). This is consistent with the features associated with the pedestal structure and that is configured to be implanted into a skull bone of the recipient.

In a feature that is different from the above-noted bone fixture 510, pedestal structure 610 is threadless over at least a majority of a longitudinal direction on bone facing surfaces. Briefly jumping to FIG. 8, the longitudinal direction is the direction of extension of arrow D1 (and distances D1 plus D2 establish the total extension of the pedestal in the longitudinal direction. Here, there are no threads over the longitudinal direction on the bone facing surfaces. Instead, there are grooves, as will be described in greater detail below.

In at least some exemplary embodiments, the pedestal structure 610 is threadless over at least 50, 55, 60, 65, 70, 75, 80, 85, 90, 91, 92, 93, 94, 95 96, 97, 98, 99, or 100% or any value or range of values therebetween in 0.1% increments (e.g., 77.7, 62.3 to 97.5, etc.) of the longitudinal direction/ longitudinal length of the pedestal.

In the embodiment of FIG. 6, the pedestal structure has a nonsmooth cylindrical face that interfaces with a skull bone. Here, grooves 665 extend about the outer circumference of the pedestal. In this exemplary embodiment, there are three grooves having relatively the same size, as can be seen. There is also a fourth groove 660, which is larger than the other groups. Groove 660 can be a composite groove that includes a ridge/bead 661 at the base of the groove, as can be seen. This feature can also be present in the grooves 665. It is also noted that a plurality of ridges/beads can be included in the grooves. Further, in some embodiments, the grooves can include sub grooves and/or a plurality of subgroups alternatively and/or in addition to the beads. It all also noted that while only grooves are depicted in the embodiment of FIG. 6, in some alternate embodiments, beads/ridges can also be included at the locations where the grooves are located (e.g., instead of the grooves) and/or in addition to one or more or all of the grooves. In an exemplary embodiment, there is at least 1, 2, 3, 4, 5, 6, 7, 8, 9, 10, 11, 12, 13, 14, 15 grooves and/or beads/ridges or any value or range of values therebetween in integer increments. Any arrangement of grooves or surface structure that can have utilitarian value can be utilized in at least some exemplary embodiments.

In an exemplary embodiment, at least one or some or all of the grooves are arranged equidistant to one another and/or are arranged symmetrically and/or are arranged such that they are rotationally symmetric about longitudinal axis 899, with the exception of, for example, the pockets 640. These grooves can have utilitarian value with respect to encouraging bone growth or otherwise enabling bone growth to grow into the grooves to further stabilize or otherwise secure the pedestal 610 after implantation. This can also be the case with respect to the pockets 640—bone can grow into the pockets over time after implantation. In this regard, in an exemplary embodiment, the pockets (or indentations in some other embodiments—the pockets of the figures are depicted as relatively large—it is conceivable that in some embodiments, less pronounced indentations can be used) can serve as irregularities for bone anchoring and/or rotational stability as well as grips for an attachment tool, as will be described in greater detail below.

Some embodiments include textured surfaces, which surface can be roughened, etc. By way of example only and not by way of limitation, laser ablation can be used to create a textured or otherwise an uneven or otherwise roughened surface to enhance osseointegration or otherwise encourage such.

It is also noted that in at least some exemplary embodiments, the surface features detailed herein, and/or other surface features can be utilized to enhance osseointegration of the bone with the pedestal. Also, in at least some exemplary embodiments, osseointegrating materials, such as titanium, can be used. Indeed, in an exemplary embodiment, the pedestal 610 is a monolithic structure, which structure can be made of titanium or a titanium alloy.

The osseointegration and/or otherwise the bone growth features associated with the teachings detailed herein can be such that the pedestal is relatively secure within the bone after 2, 3, 4, 5, 6, 7, 8, 9, 10, 11, 12, 13, 14, 15, 16, 17, 18, 19, 20, 25, 30, 35, 40, 45, or 50 weeks after implantation, or an value or range of values therebetween in one day increments. In an exemplary embodiment, it requires less than, more than, or equal to 0.1, 0.2, 0.3, 0.4, 0.5, 0.6., 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, or 6.5 Newtons, or any value or range of values therebetween in 0.01 N increments to remove the pedestal from bone after any of the aforementioned temporal periods, without a torque applied to the pedestal. Corollary to this is that in some embodiments, the pedestal is configured to enable removal of the implantable portion from the pedestal structure without removing the pedestal structure from a skull.

Thus, it can be seen that in some embodiments, the pedestal is configured to osseointegrate into bone such that about a 1, 1.5, 2, 2.5, 3, 3.5, 4, 4.5, or 5 Newton force applied in a longitudinal direction will displace the device from bone.

Briefly, the values of D3 can be less than, equal to or greater than 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6.0, 6.1, 6.2, 6.3, 6.4, 6.5, 6.6, 6.7. 6.8. 6.9. 7, 7.1, 7.2, 7.3, 7.4, 7.5, 7.6, 7.7, 7.8, 7.9, 8.0, 8.1, 8.2, 8.3, 8.4, 8.5. 8.6, 8.7, 8.8, 8.9, 9, 9.5, 10, 10.5, 11, 11.5, 12, 12.5, 13, 14, or 15 mm or any value or range of values therebetween in 0.01 mm increments. D1 or D2+D1 can be less than, equal to or greater than 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, 6.5, or 7 mm or any value or range of values therebetween in 0.01 mm increments. D2 can be less than, equal to or greater than 0.05, 0.075, 0.1, 0.125, 0.25, 0.375, 0.5, 0.6. 0.7, 0.8. 0.9, 1, 1.1, 1.2, 1.3, 1.4, or 1.5 mm or any value or range of values therebetween in 0.01 mm increments.

Thus, it can be seen that in some embodiments, the pedestal is no more than about 10, 9, 9, 7, 6, 5, or 4 mm in diameter about a longitudinal axis and/or no more than 7, 6, 5, 4 or 3 or 2 mm high in a direction of the longitudinal axis.

As noted above, the pedestal includes, in some embodiments, at least one pocket 640 extending from a distal end towards the proximal end, the pocket being configured for at least one of bone anchoring, rotational stability or tool gripping for attachment of the pedestal structure to the implantable portion (more on this below). In an exemplary embodiment, there is less than more than or equal to 1, 2, 3, 4, 5, 6, 7, 8, 9, 10, 11, 12, 13, 14, or 15 or more pockets. In some embodiments, any one or more of the pockets are arrayed symmetrically relative to the others and/or are arrayed rotationally symmetrically about the longitudinal axis 899. In an exemplary embodiment, the pockets are symmetrical with respect to a plane that is parallel to and lying on the longitudinal axis 899 and/or any other plan that is parallel to such. In an exemplary embodiment, the pockets 640 are devoid of sharp edge. In an exemplary embodiment, the pockets are devoid of sharp edges with respect to linear edges extending in the longitudinal direction and/or lateral direction. Curved edges could be sharp, while in other embodiments, the curved edges are also not sharp.

In an exemplary embodiment, the pockets extend in the longitudinal direction a distance of less, than, equal to or greater than 5, 6, 7, 8, 9, 10, 11, 12, 13, 14, 15, 20, 25, 30, 35, 40, 45, 50, 55, 60, 65, 70, 75, 80, 85, 90, 91, 92, 93, 94, 95, 96, 97, 98, 99, or 100% of D1 and/or D1+D2.

In an exemplary embodiment, the pockets collectively take up at least about an area that is less, than, equal to or greater than 5, 6, 7, 8, 9, 10, 11, 12, 13, 14, 15, 20, 25, 30, 35, 40, 45, 50, 55, 60, 65, 70, 75, 80, 85, 90, 91, 92, 93, 94, 95, 96, 97, 98, 99, or 100% of the total outer circumference area of the pedestal (i.e., not including the bottom) that faces bone and/or that is not enveloped by the implantable portion to which the pedestal is connected (more on this below). In an exemplary embodiment, the pockets collectively take up a distance, as measured on a plane that is perpendicular to the longitudinal axis, with respect to an extrapolated maximum outer circumference/outer diameter of the pedestal, that is less than, equal to or greater than 5, 6, 7, 8, 9, 10, 11, 12, 13, 14, 15, 20, 25, 30, 35, 40, 45, 50, 55, 60, 65, 70, 75, 80, 85, 90, 91, 92, 93, 94, 95, 96, 97, 98, 99, or 100% of the total outer circumference area of the pedestal (i.e., not including the bottom) that faces bone and/or that is not enveloped by the implantable portion to which the pedestal is connected (more on this below).

In some embodiments, the pedestal is machined from a cylindrical body having a circular cross-section when taken normal to the longitudinal axis thereof. In an exemplary embodiment, the grooves on the other features of the device can be established via turning the cylindrical body on a lathe or the like. The pockets, if present, can be achieved by utilizing flat headed drill bits or the like, or router bits, etc. The end result can be a thick disk-like monolithic body with uneven surfaces on all faces (top, bottom, and sides). By "thick disk-like," it is meant that the pedestal would look like a desk or the like if it was maybe a half or two thirds its height, with the same maximum outer diameter. Thus, at least some exemplary embodiments are not a disk per se, but what is referred to herein as a thick disk-like body. A cylinder might be another classification, but one might consider a cylinder to be something that is at least as high as it is thick. Thus, the pedestal is something that is in between a disk and a cylinder (under the latter definition). A thick puck is another way to classify some embodiments. Indeed, the pedestal can have scaled dimensions roughly the same as or about the same as a curling stone, such as an Olympic regulation curling stone without the handle as that which is certified for use in the 2018 or 2016 Olympics. In an exemplary embodiment, the difference between the ratio of the height to the diameter of the pedestal to that of the regulation curling stone is within 10, 20, 30, 35, 40, 45, or 50 percent. In an exemplary embodiment, implantable portion 752 is coated at least partially or fully with silicone. In some embodiments, the assembly of the pedestal with the implantable portion is such that the application of the silicone does not result in application thereof onto the pedestal. Accordingly, in at least some exemplary embodiments, the pedestal is devoid of silicone coating or other anti-osseointegrating features on at least a side or a bottom of the device. That said, silicone or some other anti-osseointegrating material/substance or surface feature can be present on the side or the bottom of the pedestal.

Figure 8:
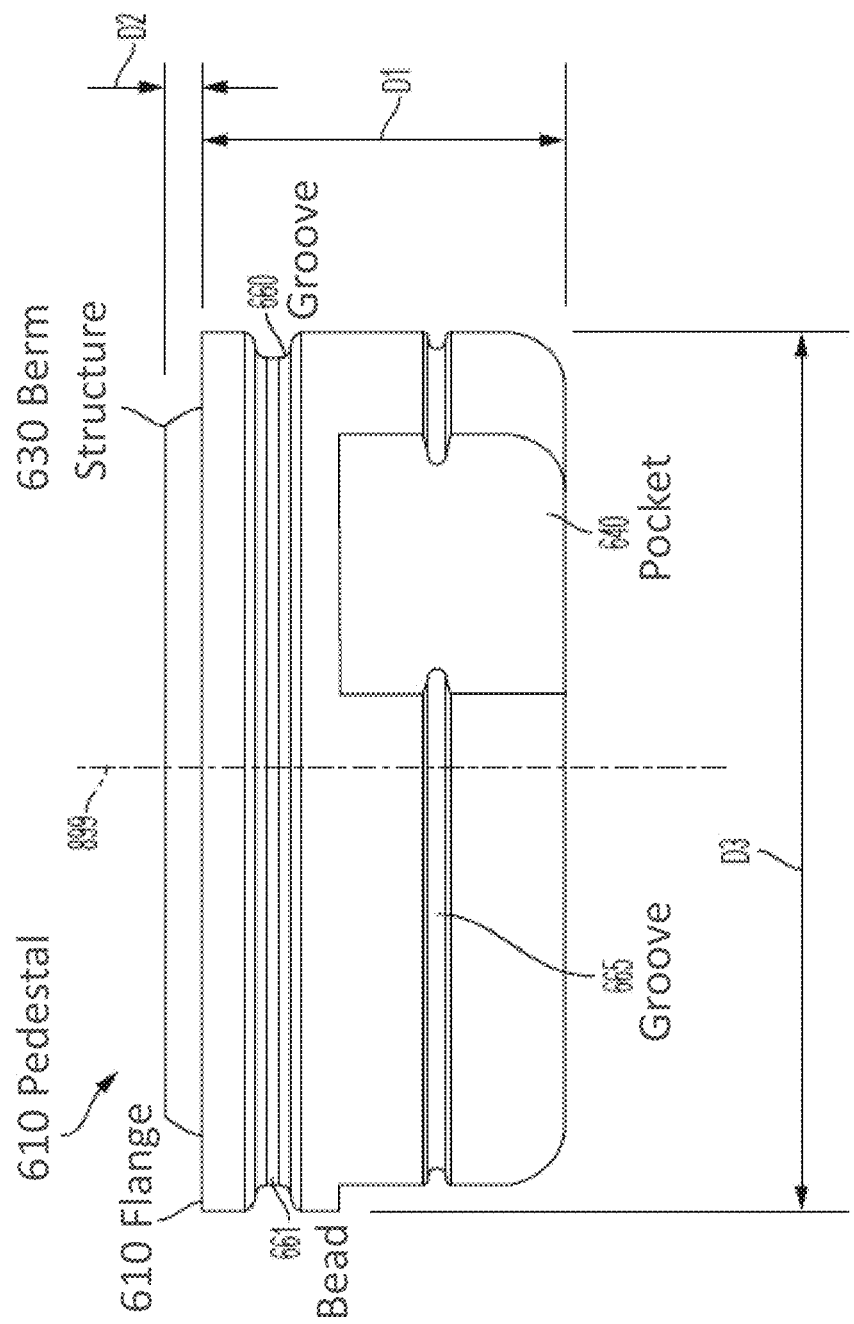
FIG. 8 depicts a side view of an exemplary pedestal according to an exemplary embodiment.

Referring to FIGS. 6 and 7 and 8, it can be seen that the pedestal structure 610 includes a ring or vertical flange 620 extending about the longitudinal axis of the pedestal at an outermost circumference thereof (in some embodiments, the ring 620 can be located in board of such), whereby inboard of the ring 620 is a valley 622, and inboard of the valley is an angled wall/berm structure 630, the valley and the angled wall extending about the longitudinal axis of the platform.

The flange, the ring, in the valley, a rotationally symmetric about the longitudinal axis. It is noted that in at least some exemplary embodiments all of the prominent structures, if not all of the structures, located on the outside of the pedestal are rotationally symmetric about the longitudinal axis. In at least some other exemplary embodiments, this is not the case.

Figure 9:
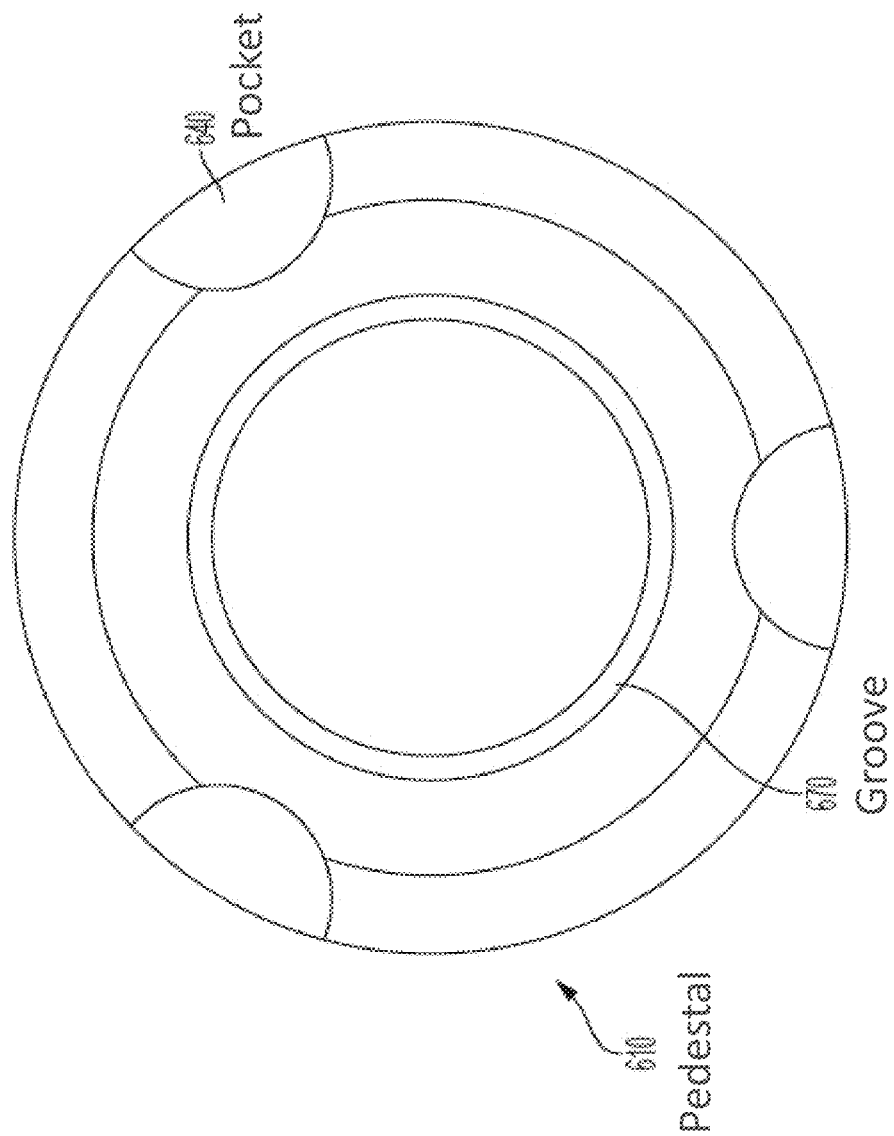
FIG. 9 depicts a bottom view of an exemplary pedestal according to an exemplary embodiment.
Figure 10:
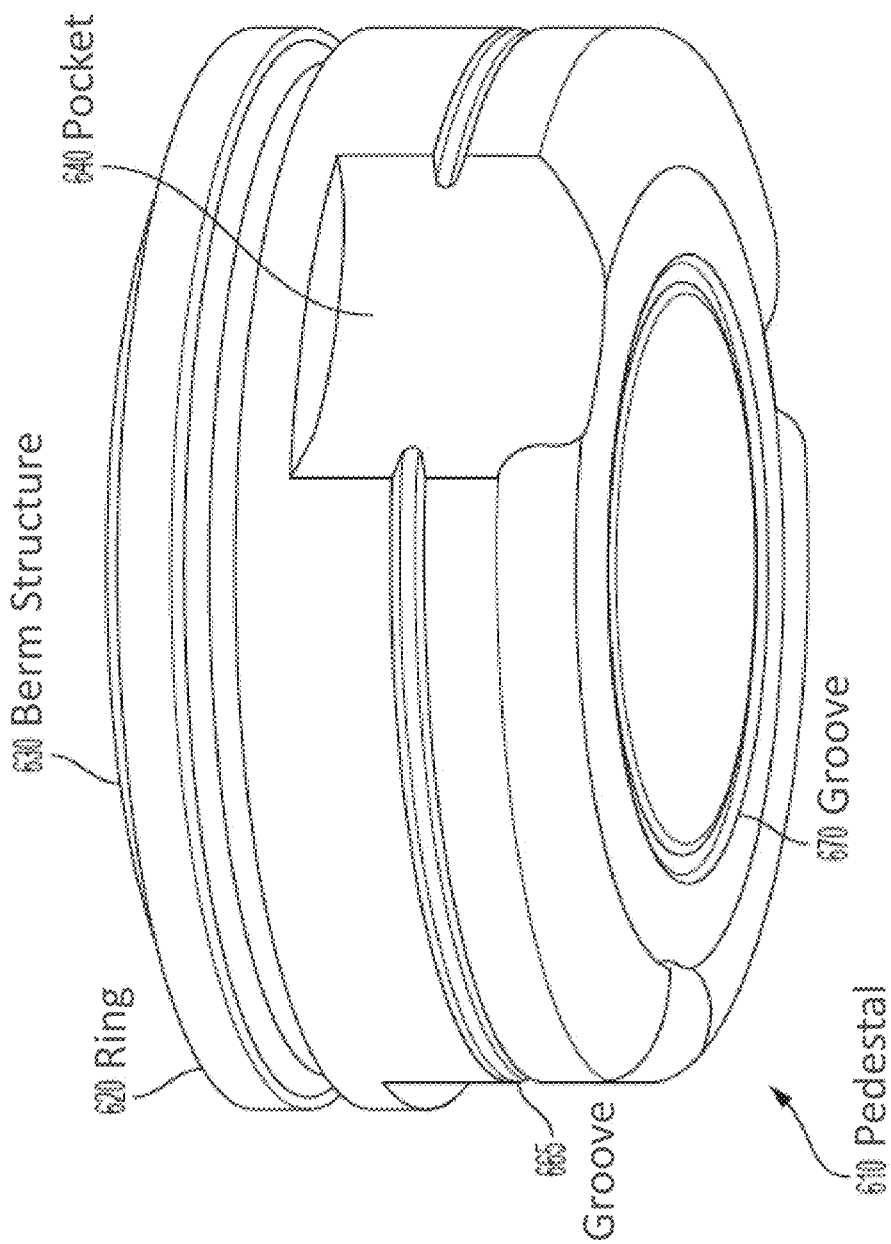
FIG. 10 presents a bottom-side view of an exemplary pedestal according to an exemplary embodiment.
Figure 11:
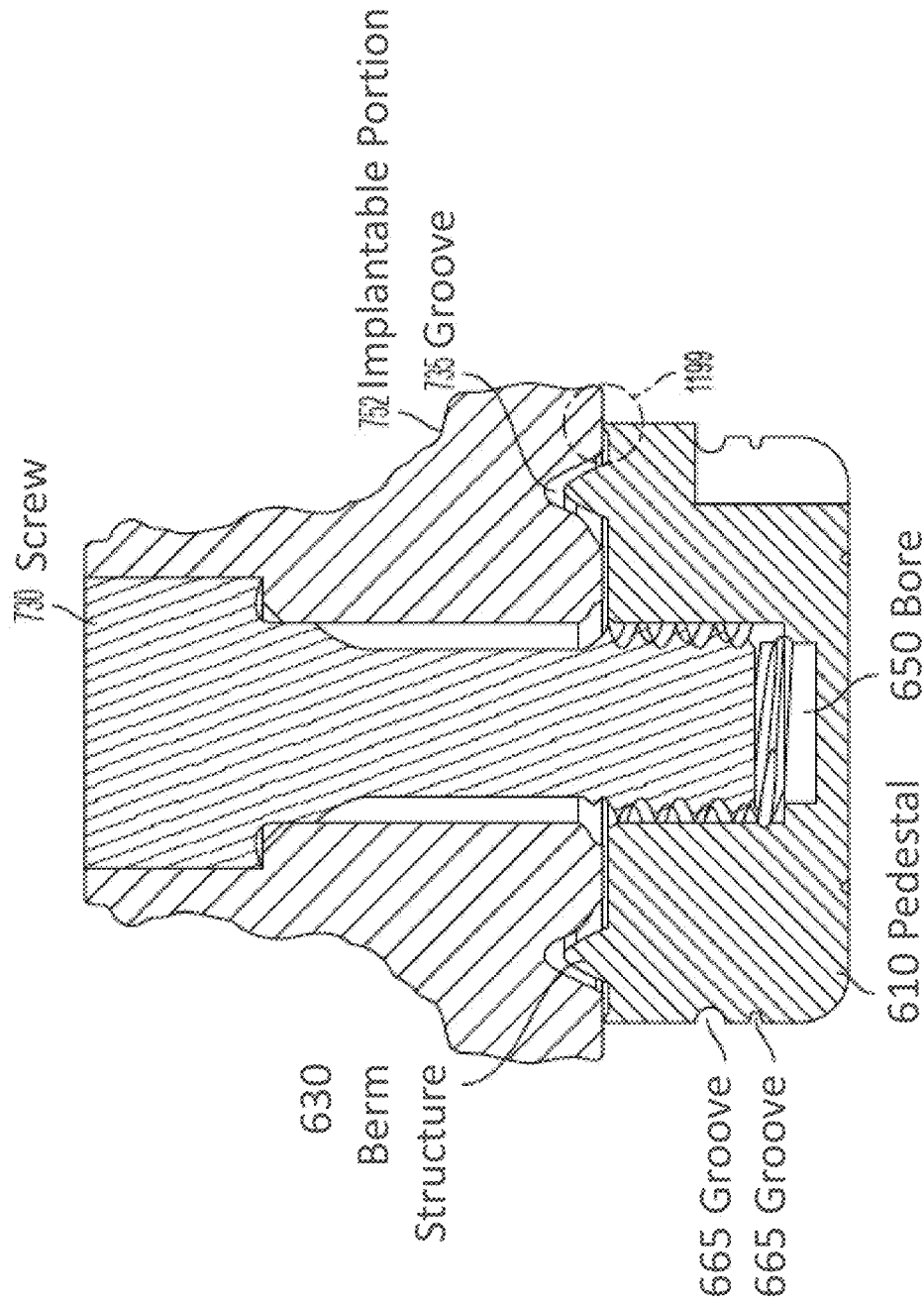
FIG. 11 presents a cross-sectional view of a portion of an exemplary embodiment of an implantable component.

The angled wall 630 can have utilitarian value with respect to acting as a guide/an alignment feature when marrying up the pedestal 610 with the implantable component 752. FIG. 7 depicts a groove 735 located on the bottom of the implantable portion 752. Additional details can be seen in FIG. 11, which depicts a close-up view of the central portions of the implantable component of the bone conduction device. As can be seen, the angled wall 630 forms a quasi-male extension that fits into the quasi-female receptacle established by the groove 735. In some embodiments, the groove and the wall are sized and dimensioned to have a slip fit, while in other embodiments, there is a clearance fit. Still further, in other embodiments, there can be an interference fit. For the most part, the utilitarian value of these components is to establish a general alignment between the pedestal 630 and the implantable portion 752. The idea is that as the screw 730 is tightened, and the pedestal and/or the implantable portion are drawn towards each other, the groove and the wall will align the two components. It is briefly noted that in at least some exemplary embodiments, the groove 735 is configured to receive the wall/berm 539 of the embodiment of FIG. 5 above. Indeed, in an exemplary embodiment, the functional relationship with respect to the groove and wall of the embodiment of FIG. 5 corresponds to that which is the case with respect to the embodiment of FIG. 6. To be clear, in at least some exemplary embodiments, the implanted portion 752 is a device that can be mated to the bone fixture of FIG. 5 and the pedestal 610 of FIG. 6. Thus, in an exemplary embodiment, the pedestals and/or the bone fixtures detailed herein can be utilized to secure the implanted portions of the active and/or passive transcutaneous bone conduction devices detailed herein. It is also noted that embodiments can have utilitarian value with respect to supporting the percutaneous bone conduction device of FIG. 2. Conversely, in at least some exemplary embodiments, the pedestal of the embodiment of FIG. 6 is decidedly not suitable or otherwise not capable of supporting a percutaneous bone conduction device, such as that of FIG. 2, at least with respect to resisting the forces that are involved with removing the percutaneous bone conduction device from the abutment during normal life (e.g., which can occur 1 or 2 or 3 times or more per day, every day or every other day for a week or a month or a year or more). In this regard, in an exemplary embodiment, when subjected to the aforementioned pulling forces for the aforementioned number of times, the pedestal might be removed from the bone, whereas the bone fixture will not be so removed from the bone. Thus, at least some exemplary embodiments of the pedestal are such that the pedestal is not for supporting a percutaneous bone conduction device and the person of ordinary skill in the art would recognize that the design and the structure of the pedestal structure is decidedly not for supporting a percutaneous bone conduction device. The pedestal includes a groove 670 at the bottom as seen in FIG. 9.

In an exemplary embodiment, the pedestal is press-fit into the hole that is ultimately established in the skull.

Accordingly, in an exemplary embodiment, the pedestal is a device that is approvable or approved by the U.S. FDA, for use with an implantable portion of a bone conduction device, such as a passive transcutaneous bone conduction device or an active transcutaneous bone conduction device, and is not approved or approvable by the FDA for use with a percutaneous bone conduction device.

Figure 20:
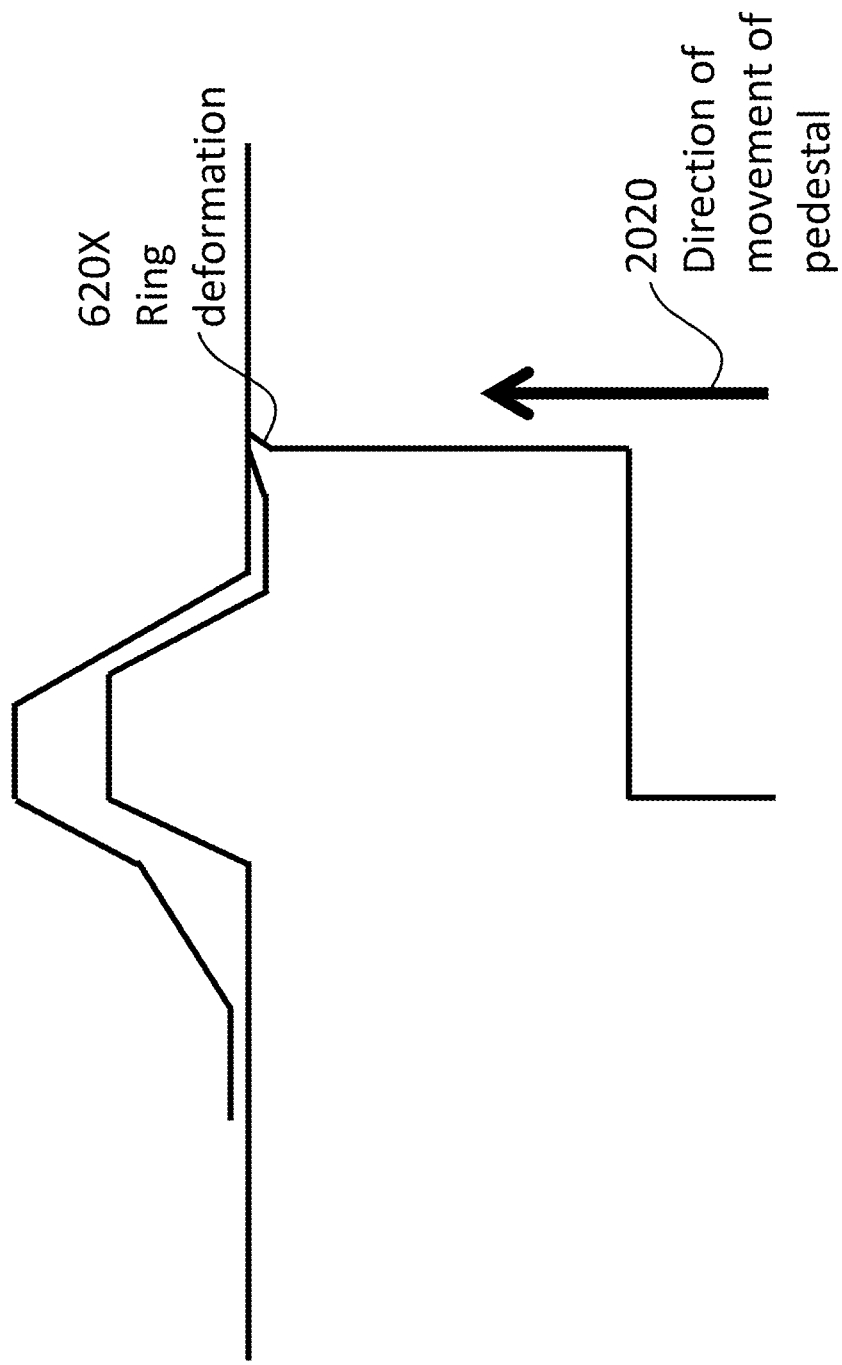

Referring back to FIG. 6, as noted above, there is an outer ring 620 that is located at the most outboard portion of the pedestal. In an exemplary embodiment, the ring 620 is configured to deform when squeezed against the bottom portion of the implantable portion 752, under a sufficient squeezing force, such as that which results from the screwing of the screw 730 into the bore 650 of the pedestal. FIG. 7 depicts a highlighted section 1199, and FIGS. 19 and 20 depict that section and an area thereabout in an enlarged format. In this regard, the ring 620 collapses or otherwise deforms with movement towards the implantable portion 752, as seen by comparing FIG. 19 to FIG. 20, where the pedestal is moved in the direction of arrow 2020, with the implantable portion 752 in a static position, where the ring 620 deforms to become 620X as seen in FIG. 20, so as to create a seal between the pedestal and the implanted portion. This seal can be an airtight seal and/or a hermetic seal. This seal can be a seal that simply impedes or otherwise slows the ingress of body fluids or otherwise bacteria or the like into the interior. That said, in some alternate embodiments, the seal is something that impedes or otherwise slows or otherwise prevents egress of material from inside to the outside. Indeed, in an exemplary embodiment, there can be a scenario where the inside is infected or otherwise contains bacteria, and the seal contains such or otherwise prevents or otherwise limits the access of the bacteria to the outside ambient environment.

Thus, in an exemplary embodiment, there is an apparatus in the form of an implantable portion of a bone conduction device, where the pedestal is a separate component from the implantable portion, and an interface between the pedestal and the implantable portion is self-sealed due to the attachment between the pedestal and the implantable portion.

Consistent with the theme herein that the pedestal is a monolithic component, the seal established by the ring 620 is part of the rest of the pedestal. In some other embodiments, the seal can be a separate component. Any arrangement that can have utilitarian value with respect to creating a seal between the two components can be utilized in at least some exemplary embodiments.

Again, while the embodiment of FIG. 6 presents the ring 620 that establishes the seal as being on the outermost periphery of the pedestal, in some embodiments, the ring can be located in board of the outermost periphery. Still further, while the embodiment of FIG. 6 presents only one ring, in some embodiments, two or three or four more rings can be utilized, and one or some or all of them can result in seals when the pedestal is squeezed against the implanted portion, thus providing potential redundancy.

It is briefly noted that element 752 represents both a portion of a passive transcutaneous bone conduction device and a portion of an active transcutaneous bone conduction device. In an exemplary embodiment, 752 is a magnet apparatus, such as a coated magnet and/or a magnet that is located in a housing, of a percutaneous bone conduction device. Still further, in an exemplary embodiment, 752 can be an actuator/housing combination of an active transcutaneous bone conduction device.

In view of the above, it can be seen that in at least some exemplary embodiments, there is an osseointegrating lateral stability device configured for removable attachment to an implantable prostatic component, such as the implantable portion of the aforementioned bone conduction devices. By "lateral stability device," it is meant that the device prevents any meaningful work effective movement in the lateral plane (e.g., tangential to the surface of the skull bone). In some embodiments, the device is only a lateral stability device in the sense that the device will not resist a longitudinal force of significance (i.e., it will pull out of the bone, even after osseointegrating/bone growth, after the aforementioned time periods disclosed herein). In some embodiments, the device resists more force in the lateral direction more than it resists force in the longitudinal direction, such as at least about 2, 3, 4, 5, 6, 7, 8, 9, 10, 11, 12, 13, 14, 15, 16, 17, 19, 19, 20, 21, 22, 23, 24, 25, 30, 35, 40, 45, 50, 55, 60, 65, 70, 75, 80, 90, 100, 125, 150, 175, 200, 250, 300, 350, 400, or more times or any value or range of values therebetween in 0.1, increments, before and/or after osseointegration and/or before and/or after the aforementioned time periods, and the device remains stable in the bone thereafter. In at least some embodiments, by way of example only and not by way of limitation, with respect to a force that is applied at a location less than or equal to 5 mm from the topmost surface of the device, at a location on aligned with the longitudinal axis, a force of 5, 6, 7, 8, 9, 10, 11, 12, 13, 14, 15, 16, 17, 19, 19, 20, 21, 22, 23, 24, 25, 30, 35, 40, 45, 50, 55, 60, 65, 70, 75, 80, 90, 100 or more Newtons or any value or range of values therebetween in 0.1, increments, before and/or after osseointegration and/or before and/or after the aforementioned time periods, can be applied such that the device will remain stable in the bone. By remains stable, it is meant that the device can be continued to be used for the purpose for which the pedestal was originally implanted immediately after being subjected to such force/without any remedial surgical operations or the like. The above values are provided with respect to an implantable component that does not have any other additional retention mechanisms, such as suturing and/or the utilization of smaller bone screws (e.g., bone screws arrayed or otherwise located about a periphery of the portion, etc.).

To be clear, it is noted that the entire implantable component that includes the pedestal is covered entirely with skin, as compared to the percutaneous bone conduction device of FIG. 2, or a component extends through the skin. There is thus utilitarian value with respect to utilizing the pedestal in that it creates a physical barrier or otherwise a physical stop to stop or otherwise reduce migration of the implantable component relative to that which would be the case in the absence of such.

Again, it is noted that in at least some exemplary embodiments, the device can have non-threaded bone interfacing surfaces extending for at least about half a longitudinal distance of the device (again, it can be almost entirely, and entirely, the longitudinal distance of the device in at least some exemplary embodiments).

In an exemplary embodiment, the device is solid with an exception of a central core component configured to receive an attachment component (e.g., screw 730).

Figure 12:
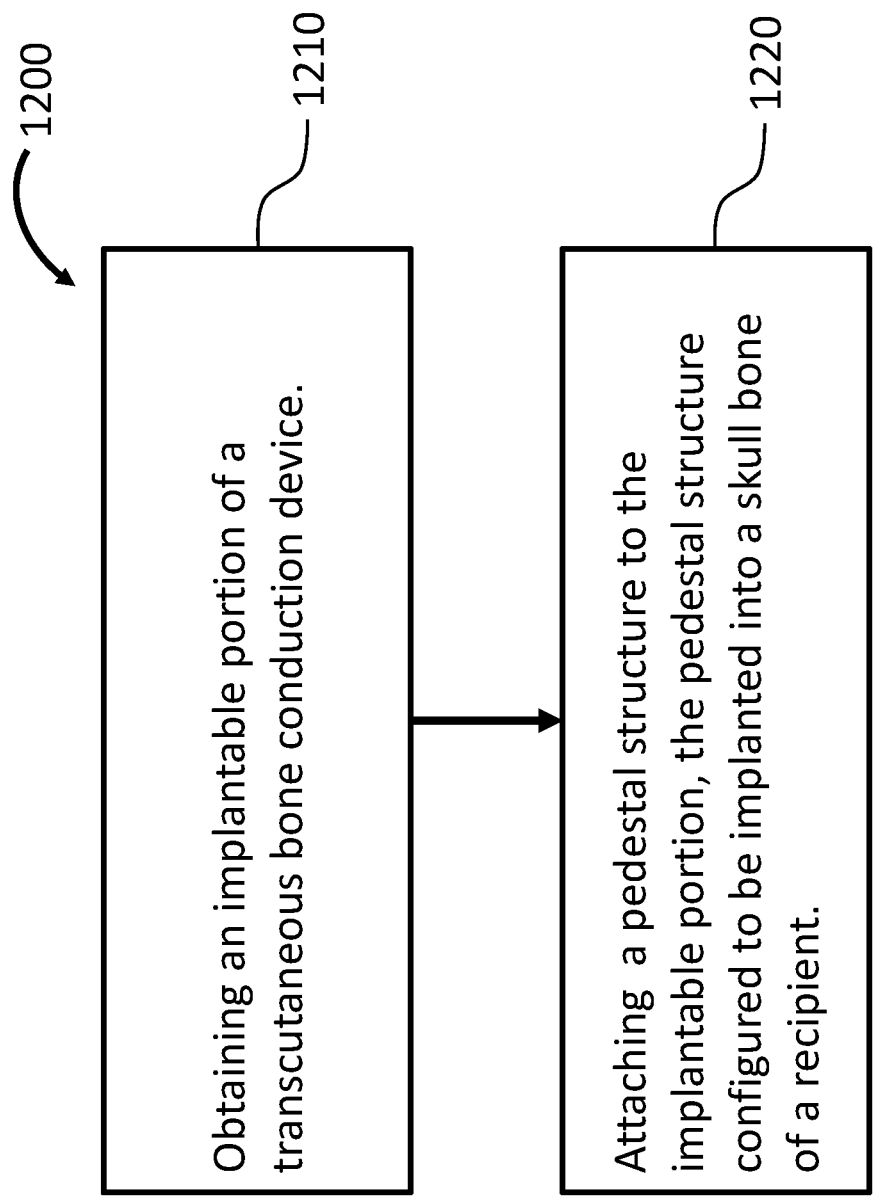
FIG. 12 presents an exemplary flowchart for an exemplary method.

FIG. 12 presents an exemplary flowchart for an exemplary method, method 1200, according to an exemplary embodiment. Method 1200 includes method action 1210, which includes obtaining an implantable portion of a transcutaneous bone conduction device. In an exemplary embodiment, the implantable portion can be the implantable portion 752, which can be, by way of example only, the magnet(s)

apparatus of the passive transcutaneous bone conduction device and/or the actuator portion of a percutaneous bone conduction device.

Method 1200 further includes method action 1220, which includes attaching a pedestal structure to the implantable portion, wherein the pedestal structure is configured to be implanted into a skull bone of a recipient.

In an exemplary embodiment, method action 1210 and/or 1220 is executed within 1, 2, 3, 4, 5, 6, or 7 days prior to implanting the implantable portion. That said, in a variation of this method, the obtaining action is executed later.

In an exemplary embodiment, method action 1210 and/or 1220 is executed temporally proximate, such as in close temporal proximity to the action of implanting the implantable portion into a recipient. In some embodiments, method action 1210 and/or 1220 is executed the same day as the operation that implants the implantable portion into the recipient. In an exemplary embodiment, method action 1210 and/or 1220 is executed within 0.1, 02, 0.25, 0.5, 0.75, 1, 1.5, 2, 2.5, 3, 3.5, 4, 4.5, 5, 5.5, 6, 7, 8, 9, 10, 11, 12, 13, 14, or 15 hours, or any value or range of values thereof in 0.1 hour increments of the completion of the drilling of a hole into the skull for the pedestal (e.g., 1 hour before or 0.25 hours after). Indeed, in an exemplary embodiment, method action 1210 and/or 1220 is executed while the hole was being drilled.

Thus, as can be seen, in at least some exemplary embodiments, there is a method where the action of implanting the assembly of the pedestal and the implantable portion that is implantable in a skull of a human is executed in temporal proximity, such as in close temporal proximity to the action of attaching the pedestal to the implantable portion.

Still further, in an exemplary embodiment, the method includes removing the pedestal and/or the implantable portion from a hermetically sealed package/sterilized enclosure, wherein the pedestal and the implantable portion are not connected to one another at the time of opening of the package/enclosure containing the pertinent component. In an exemplary embodiment, the action of opening and/or removing the components from the aforementioned packaging/enclosure is executed in a healthcare facility. In an exemplary embodiment, the action of connecting the pedestal to the implantable portion is executed within 0.1, 0.2, 0.25, 0.5, 0.75, 1, 1.5, 2, 2.5, 3, 3.5, 4, 4.5, 5, 5.5, 6, 7, 8, 9, 10, 11, 12, 13, 14, or 15 hours, or any value or range of values thereof in 0.1 hour increments of the opening of the aforementioned packages/enclosure and/or within 0.25, 0.5, 0.75, 1, 1.5, 2, 2.5, 3, 3.5, 4, 4.5, 5, 5.5, 6, 7, 8, 9, 10, 11, 12, 13, 14, or 15 hours, or any value or range of values thereof in 0.1 hour increments of the completion of the drilling of a hole into the skull for the pedestal. Indeed, in an exemplary embodiment, the packaging/enclosure is opened while the hole was being drilled.

In an exemplary embodiment, the implantable components are provided as a kit or the like that include both a pedestal and a bone fixture/bone screw, such as, respectively, the pedestal of the embodiment of FIG. 6 and the bone screw of the embodiment of FIG. 5. In this manner, the surgeon or other healthcare professional can choose between the two types of anchoring components. That is, in an exemplary embodiment, at the time the surgery, the surgeon can pick the anchoring apparatus that he or she would rather use or otherwise believes is most appropriate for a given recipient at that current time. That said, in an alternate embodiment, the implantable portion can be shipped with one or the other anchoring components based on the order from the hospital or other healthcare facility. In either scenario, the attachment of the pedestal to the implantable portion can occur within the aforementioned temporal period of times.

Thus, in an exemplary embodiment, there is a method as detailed above that further includes, prior to the action of attaching the pedestal structure to the implantable portion (method action 1220), the action of choosing between the pedestal structure and a screw bone fixture. In an exemplary embodiment, the action of choosing between the pedestal structure and the screw bone fixture are choices between the two that are available to a person attaching the pedestal structure at least one of the time of osseointegrating with the time of attaching.

In some embodiments, there is a method that includes an action of drilling a hole into a skull using a drill. The drill that is utilized is a high-speed drill operated at high speeds. In some embodiments, the drill that is utilized is a low-speed drill operated at low speeds. In an exemplary embodiment, the drill is a drill that is not capable of being operated at a high-speed or is not capable of being operated at low-speed. In some embodiments, the action of drilling a hole is executed utilizing a drill that is only a low-speed drill or only a high-speed drill. That is, no low-speed drill is utilized, or no high-speed drill is utilized. Indeed, in an exemplary embodiment, no low-speed drill usable for the procedure of drilling the hole in the skull is accessible in the healthcare facility where the action of drilling a hole is executed.

In some embodiments, the drill that is utilized is operated at a speed of and/or has a maximum RPM of no more than or at least more than 3, 4, 5, 6, 6, 7, 8, 9, 10, 11, 12, 13, 14, 15, 16, 17, 18, 19, 20, 25, 30, 35, 40, 45, or 50 thousand RPM. In an exemplary embodiment, the facility where the action of drilling a hole is executed does not have access to a drill motor that is usable for the procedure that can operate at and/or higher than or lower than 3, 4, 5, 6, 6, 7, 8, 9, 10, 11, 12, 13, 14, 15, 16, 17, 18, 19, 20, 25, 30, 35, 40, 45, or 50 thousand RPM.

In some exemplary embodiments, after the action of drilling a hole but before the action of placing the pedestal into the hole, the drilled hole is reamed. (It is noted that this can also be the case with respect to methods of implanting the bone screw of FIG. 5, in some embodiments.)

There can be utilitarian value with respect to utilizing a high-speed drill. It is noted that in at least some exemplary embodiments, the utilization of a high-speed drill can induce a scenario where the speed of the drill results in the generation of heat which can damage or otherwise kill bone tissue. This scenario may not necessarily be the case with respect to the utilization of a low-speed drill, or, more accurately, the likelihood of damaging the bone is much lower with respect to the utilization of a low-speed drill relative to the utilization of a high-speed drill. Accordingly, there is utilitarian value with respect to utilization of a low-speed drill. That said, the teachings detailed herein can provide for the utilization of a high-speed drill which can be desirable because high-speed drills drill faster in at least some exemplary scenarios. In this regard, a smaller hole can be drilled for the pedestal according to the teachings detailed herein, as opposed to, for example, the bone fixture. Because the hole is smaller, the maximum outer velocity of the drill bit will be lower than that which would be the case for a given RPM if the hole was larger, all other things being equal. Accordingly, the teachings detailed herein include the utilization of a high-speed drill operated at relatively high speeds.

In some embodiments, the action of drilling the hole for the pedestal is executed by drilling a small guide hole, and then reaming out a larger hole.

In some embodiments, the method further includes, after drilling a hole (which can also include after reaming the hole), placing the pedestal into the hole during an implantation process so as to implant the pedestal and the implantable portion into a head of the skull. In some embodiments, the hole has a diameter equal to the average (mean, median and/or mode) and/or the maximum outer diameter of the pedestal. In an exemplary embodiment, the hole has a diameter that is within (greater than or less than) 0.0005, 0.0006, 0.0007, 0.0008, 0.0009, 0.001, 0.0012, 0.0014, 0.0016, 0.0018, 0.0020, 0.0025, 0.003, 0.0035, 0.0040, 0.0045, 0.0050, 0.006, 0.007, 0.008, 0.009, 0.01, 0.015, 0.2, 0.025, 0.03, 0.035, 0.04, 0.05, 0.06, 0.07, 0.08, 0.09, 0.1, 0.11, 0.12, 0.13, 0.14, 0.15, 0.16, 0.17, 0.18, 0.19, 0.20, 0.21, 0.22, 0.23, 0.24, or 0.25 mm, or any value or range of values therebetween in 0.001 mm increments of the aforementioned diameters of the pedestal. Thus, in some embodiments, the hole is a slip fit and/or a slight interference fit and/or a slight clearance that with respect to the pedestal.

It is noted that in an exemplary embodiment, no part of the pedestal cuts into bone during the implantation process. All cutting is done with respect to the drill and/or reaming operations. In an exemplary embodiment, no portion of the pedestal extends into the bone with respect to the lateral direction beyond that of any other portion of the pedestal (which would be the case with the bone screw of FIG. 5, where the threads would extend into the bone). In an exemplary embodiment, the pedestal pushes the bone outward in the radial direction an amount that is substantially even over the length of the pedestal (as opposed to a threaded body).

In some embodiments, the hole that is drilled/reamed has a depth that is within 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.20, 0.21, 0.22, 0.23, 0.24, 0.25, 0.3, 0.35, 0.4, 0.45, 0.5, 0.55, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.25, 3.5, 3.75, 4.0, 4.25, 4.5, 4.75, or 5 mm of the maximum values of D1 or D1+D2.

It can be seen that in at least some embodiments, the teachings detailed herein provide reproducible method actions for treatment of a plurality of recipients. Accordingly, in at least some exemplary embodiments, one or more of the actions of attaching, drilling, placing and/or reaming are executed at least 10, 15, 20, 25, 30, 35, 40, 45, 50, 55, 60, 65, 70, 75, 80, 85, 90, 95, 100, 125, or 150 times or more in association with respective different recipients of respective pedestals and implantable portions.

Figure 13:
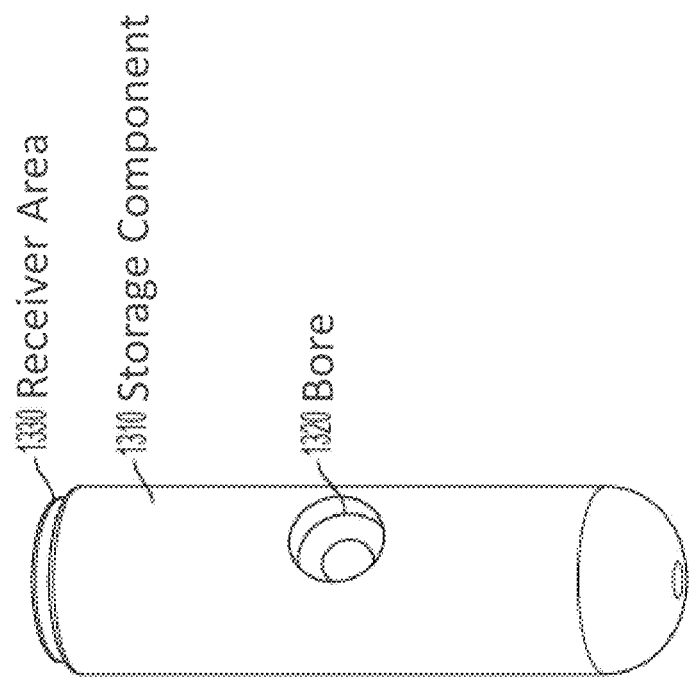
FIGS. 13-16 presents diagrams presenting an exemplary packaging arrangement according to an exemplary embodiment.

It is noted that some embodiments of the teachings detailed herein include packaging and/or kits that have utilitarian value with respect to the assembly of the pedestal to the implantable portion. As noted above, in some embodiments, some or all of the components of the implantable component are package or otherwise enclosed in a hermetically sealed/sterilized enclosure. In some embodiments, the pedestal is shipped with the implantable portion in a single package or as a collection of packages in the same shipping container or the like, but in both instances or in all instances, the pedestal is not attached to the implantable portion. Some embodiments include a storage component (any component that functions to aid in the storage capacity of the pedestal and/or the implantable portion) that supports or otherwise contains partially or fully the pedestal. Briefly, FIG. 13 presents such a storage component. Here, storage component 1310 is in the form of a screwdriver handle or other torque applying device. The screwdriver handle has a bore 1320 that is configured to receive the screw 730 that is utilized to connect the pedestal to the implantable portion (not shown in FIG. 13). In an exemplary embodiment, the screw can be slipped fitted or clearance fitted into the bore 1320 and held in place with tape or an easily removed adhesive. In other embodiments, the screw is fitted into the bore 1320 in an interference fitted and/or a screwed and manner. In this regard, in an exemplary embodiment, the handle 1310 can be made of plastic or the like which can be easily threaded. That said, in an alternative embodiment, the handle can be made of a non-dissimilar metal from the material of the pedestal and/or the screw or a stronger material than plastic.

Figure 14:
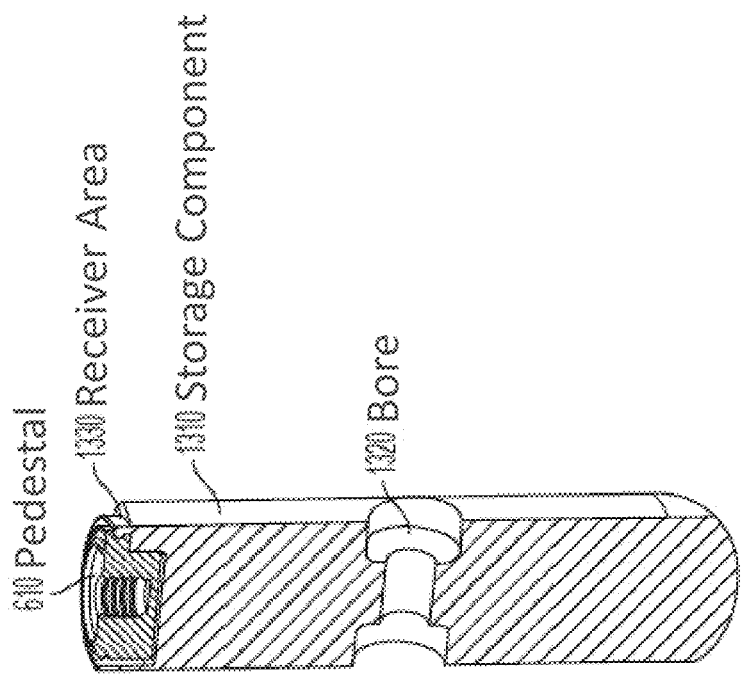

In any event, in an exemplary embodiment, at the time of connecting the distal to the implantable portion, the screw 730 is removed from bore 1320 and placed through the through bore in the implantable portion. Further, the storage component 1310 includes a receiver area 1330 at the top thereof. FIG. 14, a cross-sectional view through the storage component 1310 and the pedestal 610, shows the pedestal 610 received into the receiver area 1330. In an exemplary embodiment, a cap with a like is fitted over the receiver area 1330, which cap can interference fit or snapfit, for example, onto the outer surface of the receiver area 1330.

In an exemplary embodiment, the receiver area 1330 is sized and dimensioned so that the receiver area can be placed against or otherwise in close spatial proximity to the bottom surface of the implantable portion. In an exemplary embodiment, the screw 730 is screwed into the threaded bore of the pedestal 610 while the pedestal is located in the receiver area. That said, in an alternate embodiment, the pedestal 610 can be removed from the receiver area and placed onto the threads of the screw 730 in a finger tight manner (e.g., started by hand). In both scenarios, the handle 1310 is used to apply one of torque and/or apply a counter torque to the pedestal 610 while the screw 730 as being screwed into the pedestal.

Figure 15:
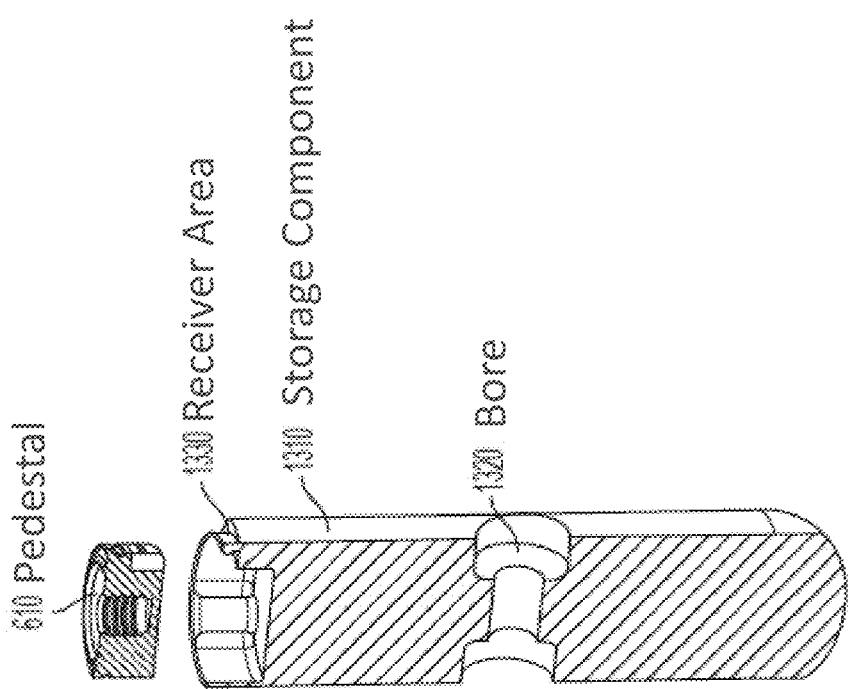
Figure 16:
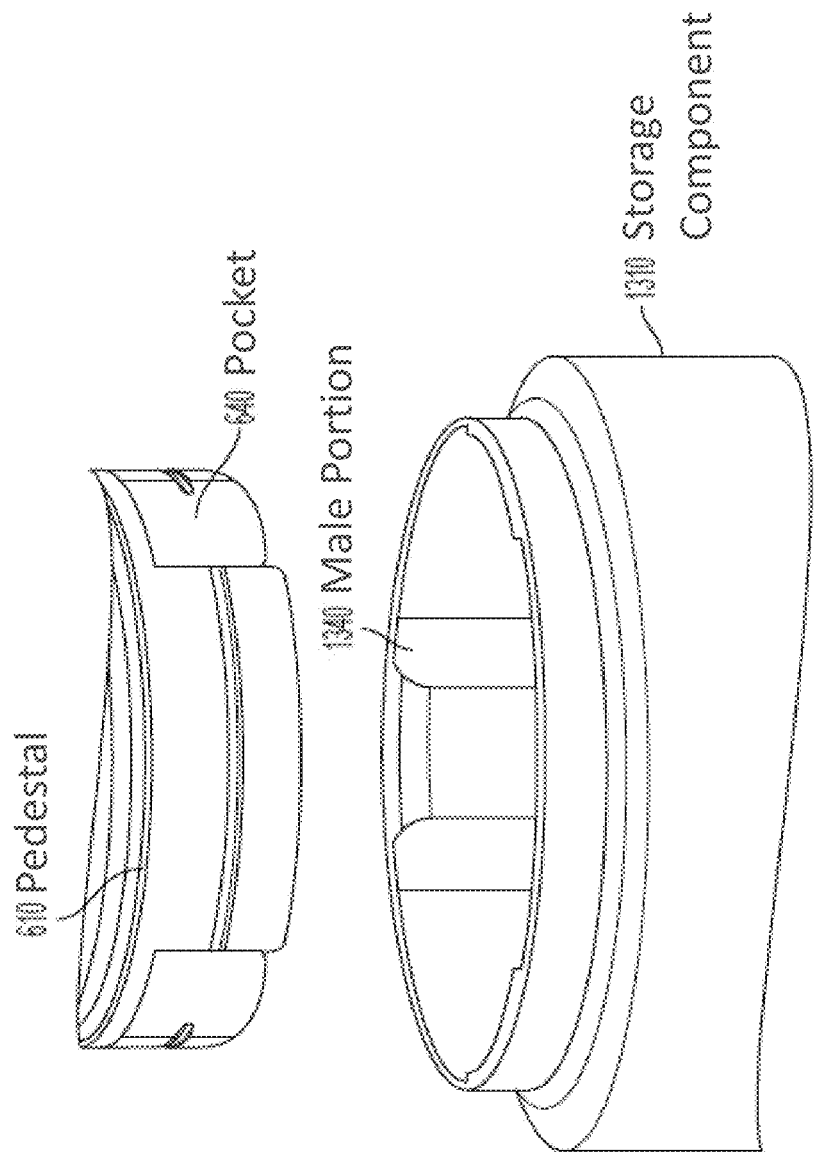

FIG. 15 depicts the pedestal 610 being removed from the receiver area 1330 of the handle 1310. As can be seen, and with further detail depicted in FIG. 16, the receiver area 1330 includes male portions 1340 which fit into the pockets 640 of the pedestal. In an exemplary embodiment, the male portions 1340 react against the torque that results from squaring the screw 730. In this regard, the male portions 1340 located in the receptacle of the receiver area 1330 are sized and dimensioned so as to permit the pedestal structure 610 to be slip fit and/or interference fitted and/or slightly clearance fitted into the receptacle while preventing the pedestal 610 from rotating due to the torque applied to the screw 730 which is transferred to the pedestal 610.

In an exemplary embodiment, the surgeon and/or a healthcare professional holds the handle 1310 in one hand, while a torque is applied with an Allen wrench or the like to the screw 7302 screw the screw 730 into the pedestal 610, thus connecting the pedestal 610 to the implantable portion 752 or the like.

Accordingly, in an exemplary embodiment, there is a kit, comprising the pedestal and/or the components of the pedestal and the implantable portion of the bone conduction device and/or the screw that attaches the two together. This kit can include a storage component in which is received at least partially the pedestal. Again, in an exemplary embodiment, the storage component can correspond to the handle 1310 with or without a cap over the above. It is noted that the pedestal 610 can be interference fitted or snap fitted or adhesively retained into the receptacle of the receiver area. Any device, system, and/or method of maintaining the pedestal in the receiver area that will enable relatively easy and/or otherwise utilitarian removal thereof from the storage component can be utilized in at least some embodiments.

Consistent with the teachings above, the storage component can be configured in a form of a hand torque acting and/or reacting device configured to apply and/or prevent, respectively, a rotation of the pedestal upon the screwing of a component, such as screw 730, into the apparatus.

Further, in some embodiments, the storage component can be in the form of a screwdriver handle as shown. Alternatively, the storage component can be in the form of a knob or a T handle, or a cube. Indeed, in an exemplary embodiment, the storage component is not necessarily a component that can be gripped easily by hand. It instead can be a component that can be placed into a vice. In fact, in some embodiments, the storage component has a clamp device that enables the storage component to be clamped to a table or the like for the purpose of reacting against any torque that would be applied thereto as a result of the spring operation.

Still, in an exemplary embodiment, the pedestal is located in a recess at an end of the handle, as discussed above. In some embodiments, the pedestal includes female portions on an outer circumferential surface thereof (e.g., pockets 640), which female portions receive male portions of the handle (portions 1340) that protrude axially and radially in the recess of the handle. Also as can be seen, in some embodiments, this handle can include a hole in the handle extending in a lateral direction of the handle (hole 1320), in which a screw device is located, which screw device is configured to be screwed into a threaded interior whole of the pedestal so that the implantable component can be screwed to the pedestal. Again, in some embodiments, the handle 1310, the pedestal 610, and/or the screw 750 can be located in a hermetically sealed package. Alternatively, and/or in addition to this, the receiver area can be hermetically sealed and/or the area that encloses the screw device can be hermetically sealed (e.g., a shrink wrap can be placed over the ends of the bore 1320, or plugs can be so placed over the bore after and/or during a sterilization process). In some embodiments, the implantable portion is provided along with the pedestal in the same packaging, whether hermetically sealed together or separately sealed. That said, in some alternate embodiments, the package only contains the handle, the pedestal and/or the screw 750. In this regard, the packaging is separate from the implantable portion 754. This might be the case where, for example, a particular hospital or other healthcare facility or other healthcare professional does not want to use the bone fixture/bone screw of the embodiment of FIG. 5, whereas others would want to use such as opposed to utilizing the pedestal. Accordingly, a supply of implantable portions 752 can be provided, and a separate supply of the anchoring portions can be provided, whether those be the pedestal, or the screw were combination of the two.

Corollary to the above, in an exemplary embodiment, there is a method including any one or more the method actions detailed herein, that includes obtaining a packaging in which the pedestal structure was stored and is supported thereby at the time of obtaining the pedestal. Further, in an exemplary embodiment, the method includes using the packaging to at least one of applied torque or a counter torque to the pedestal structure during the action of attaching.

In some embodiments, with respect to lateral sides of the pedestal, an average variation of a surface distance from the longitudinal axis is no more than 1.5, 1.4, 1.3, 1.2, 1.1, 1.0, 0.9, 0.8, 0.7, 0.6, 0.5, 0.4, 0.3, 0.2, or 0.1 mm, or any value or range of values therebetween in 0.01 mm increments, including or excluding the pockets, if present.

Figure 21:
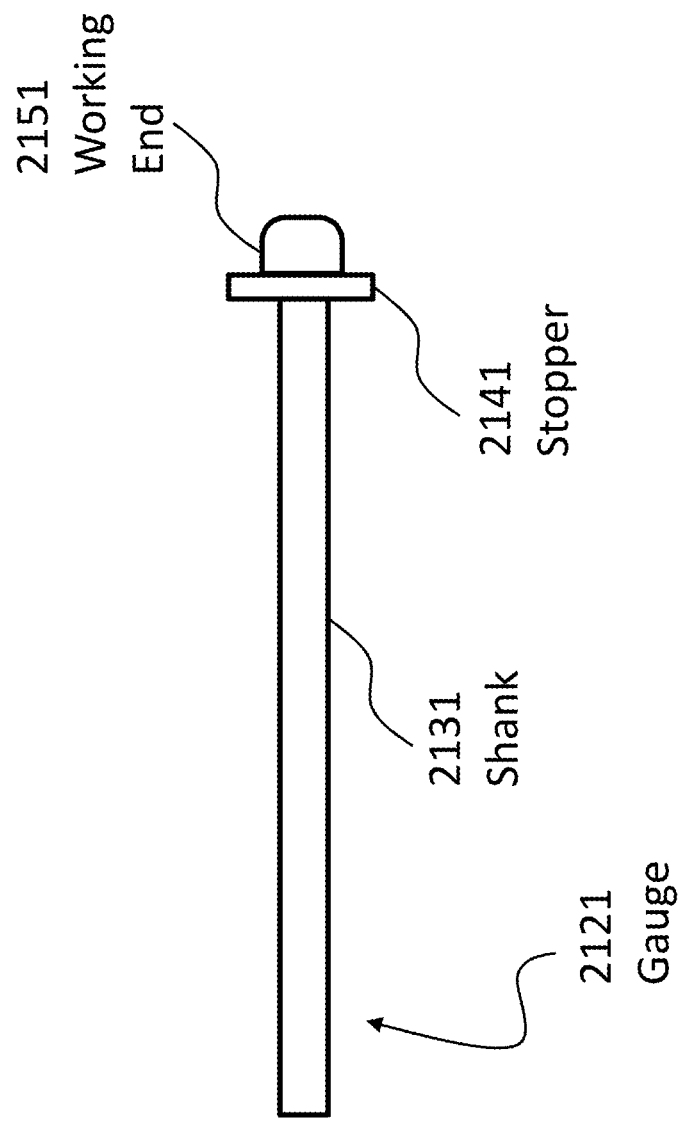
FIG. 21 depicts an exemplary gauge according to an embodiment.

It is also noted that some embodiments include a sizing gauge, which can be included in any of the kits disclosed herein, configured to size a hole in a skull for confirmation that the hole size is suitable for the device. The gauge 2121 (FIG. 21) can have an elongate shank 2131 or otherwise a device that serves as a handle (or, more accurately, a fingerle, as in some embodiments, it is gripped with a forefinger and a thumb), and includes a stopper 2141 and a working end 2151, as seen in FIG. 21. In an exemplary embodiment, the working end 2151 is a plastic body having outer dimensions corresponding to that of the pedestal that is to be inserted, save for, for example, a rounded front end in some embodiments, as seen. That said, in an alternate embodiment, the working end 2151 can be over dimensioned or under dimensioned relative to the pedestal that is to be inserted into the hole in the skull. In an exemplary embodiment, the gauge has the same or similar dimensions as the pedestal. Any dimensioning that can have utilitarian value with respect to providing an indication to a surgeon or the like that the hole is of proper size (not too big and/or not too small) for the pedestal can be utilized in at least some exemplary embodiments. In an exemplary embodiment, the gauge 2121 is a plastic monolithic component.

Thus, in an exemplary embodiment, there is a method includes any one or more the method actions detailed herein, that further includes utilizing a gauge to verify correct drilling and/or reaming dimensions prior to insertion of the pedestal into the hole.

It is noted that in some embodiments, bone cement, bone substitute, and/or glue or any other biocompatible substance that can be utilized in a utilitarian manner is utilized to aid in securement of the pedestal in the hole. That said, in some embodiments, there is no such substance that is utilized.

It is noted that in an exemplary embodiment, there is a method that includes changing a transcutaneous bone conduction device from an active transcutaneous bone conduction device to a passive transcutaneous bone conduction device, and, in an alternative exemplary embodiment, there is a method that includes changing a transcutaneous bone conduction device from a passive transcutaneous bone conduction device to an active transcutaneous bone conduction device. In these embodiments, initially, the first type of device is secured or otherwise stabilized in the bone with a pedestal according to the teachings detailed herein. In an exemplary embodiment, the implantable portion, which can be a magnet in the case of a passive transcutaneous bone conduction device or an actuator in the case of an active transcutaneous bone conduction device, is removed from the pedestal without removing the pedestal from the bone. Indeed, in an exemplary embodiment, no implantable portion is replaced at least for a time being. In an exemplary embodiment, the access to the skull is sewn up and days or weeks or months go by without placing a new implantable portion therein. That said, in an alternate embodiment, during the operation that removes the implantable portion, another component is added and attached to the pedestal without removing the pedestal from the bone. In the case of the conversion from the passive change continues bone conduction device to an active transcutaneous bone conduction device, the implantable portion that is replaced is an actuator enclosed in a housing, for example. In an exemplary embodiment, the actuator is screwed to the pedestal, whether that be via the utilization of an integrated screw body with the housing, or whether that be with a separate screw according to the teachings detailed herein. In an exemplary embodiment where the conversion is from an active transcutaneous bone conduction device to a passive transcutaneous bone conduction device, the actuator and other components removed, and in its place is provided a magnet, which is attached to the pedestal in any manner that can have utilitarian value.

Accordingly, in an exemplary embodiment, there is a method that includes removing the implantable portion 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 months or years or any value or range of values therebetween in one day increments after the implantation of the removed implantable portion and replacing the implantable portion with another implantable portion (note that in some embodiments, a change in the type of device need not necessarily be the case—a failed or an obsolete actuator could be replaced with a new and improved actuator, etc.), all without disturbing or otherwise moving the pedestal relative to the bone.

It is noted that in at least some exemplary embodiments, the action of attaching and/or removing the implantable portion is executed without applying any separate counter torque to the pedestal beyond that which results from the bone and/or any other components that were added at the initial time of implantation and remain implanted in the recipient, barring any dissolving feature (e.g., sutures that might be dissolved). To be clear, in an exemplary embodiment, the pedestal and/or the screw and/or the implantable portion are sized and dimensioned so as to reduce if not eliminate the likelihood that the torqueing action applied with respect to removal of the screw results in sufficient torque to the pedestal that could result in movement of the pedestal from the bone.

In an exemplary embodiment, the grooves are configured to promote growth of the recipient's skull bone after implantation of the pedestal into the skull. In this regard, the grooves constitute at least one structural surface feature configured to promote the growth of bone.

In a similar vein, some exemplary embodiments of some exemplary pedestals include a porous-solid scaffold that is configured to promote growth of the recipient's skull bone. More particularly, in an exemplary embodiment, the spaces in between the grooves and/or the grooves include a portion that includes such a porous-solid scaffold.

Figure 17:
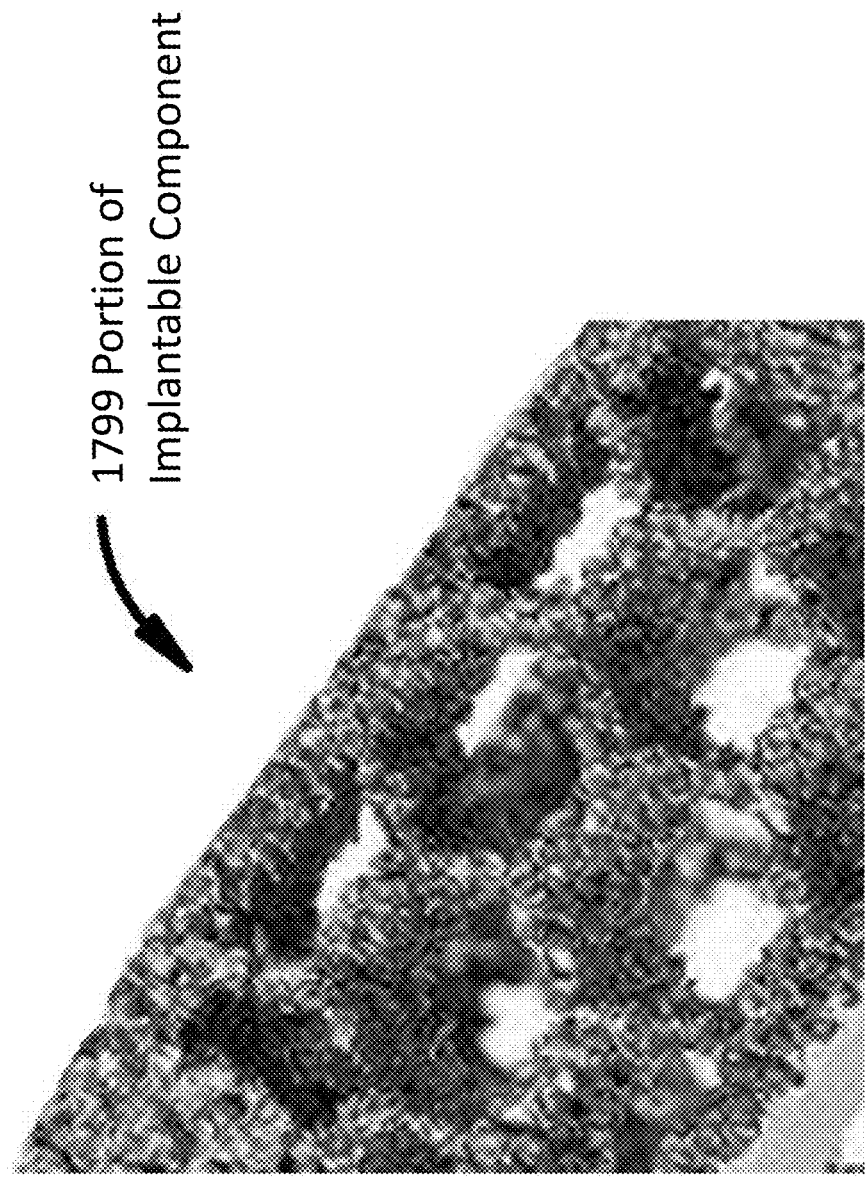
FIG. 17 depicts an exemplary embodiment of a structure of a portion of the exemplary bone fixture.

FIG. 17 illustrates an exemplary structure usable in at least some embodiments of some exemplary pedestals. Specifically, FIG. 17 depicts an implantable component has a trabecular (bone-like) structure/a 3-dimensional structure. More specifically, FIG. 17 illustrates an enlarged view of a portion 1799 of a body of an implantable component configured to be implanted adjacent to a recipient's bone and is configured to promote bone ingrowth and/or ongrowth to interlock the implantable component with the recipient's bone. In the embodiments of FIG. 17, the portion 825, as well as the remainder of the osteoconductive implantable component, is a porous-solid scaffold that comprises an irregular three-dimensional array of struts. In an exemplary embodiment, the irregular scaffold of FIG. 17 allows for vascular and cellular migration, attachment, and distribution through the exterior pores into the scaffold. The porous solid scaffold FIG. 17 may be formed, for example, from a solid titanium structure by chemical etching, photochemical blanking, electroforming, stamping, plasma etching, ultrasonic machining, water jet cutting, electrical discharge machining, electron beam machining, or similar process.

Embodiments utilizing the structure of FIG. 17 provide an osteoconductive implantable component that has a porous structure to facilitate bone ingrowth and/or ongrowth so as to interlock the implantable component with the recipient's skull bone. In the above embodiments, the bottom (i.e., bone-facing) surface has the same structure as the rest of the implantable component (i.e., generally porous).

Hereinafter, such structures are referred to as a porous-solid scaffold. Some exemplary embodiments of a porous-solid scaffold that can be utilized with embodiments detailed herein and/or variations thereof are disclosed in U.S. patent application Ser. No. 14/032,247, filed on Sep. 20, 2013, naming Goran Bjorn and Jerry Frimanson as inventors.

In an exemplary embodiment, porous-solid scaffold forms at least a portion of the surface of the pedestal. In an exemplary embodiment, the porous-solid scaffold extends a certain depth below the surface of the pedestal. That is, in an exemplary embodiment, the entire implant is not a porous-solid scaffold.

Figure 18A:
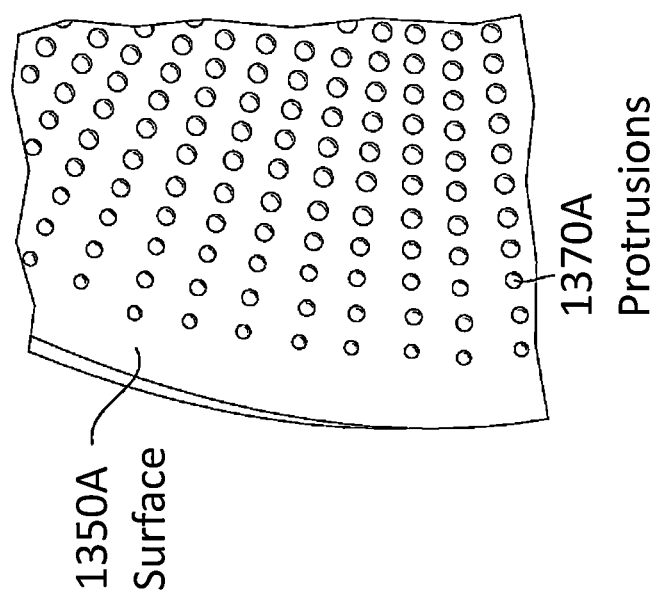
FIGS. 18A-18K depict exemplary surface discontinuities according to an exemplary embodiment.
Figure 18B:
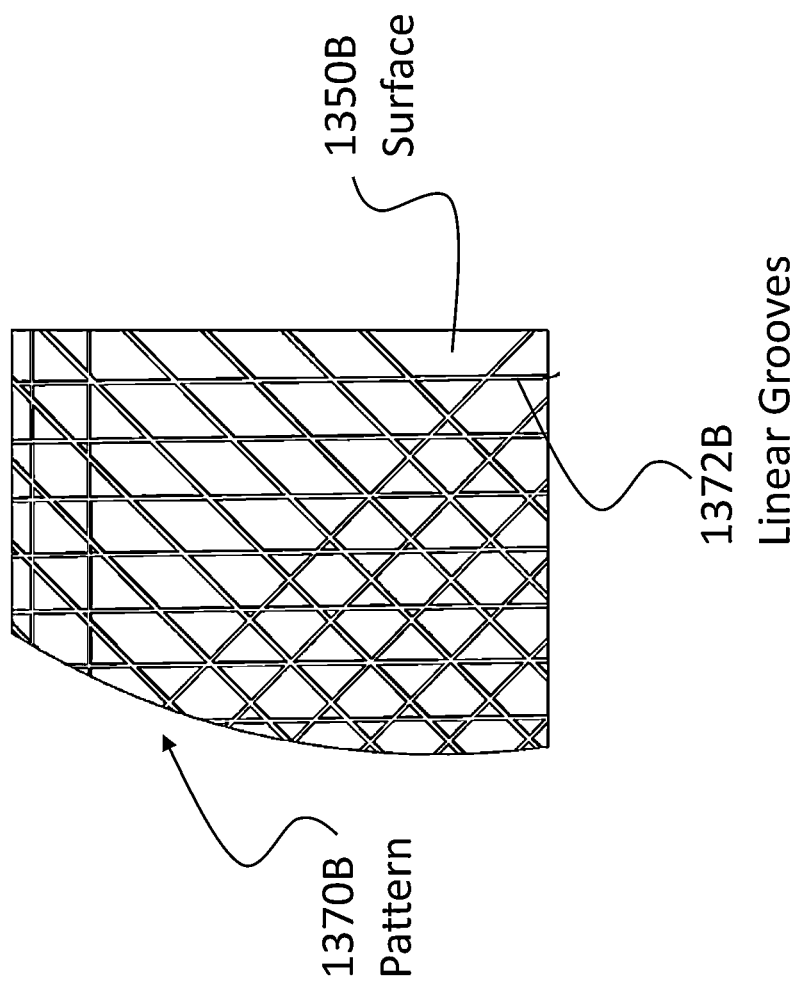
Figure 18C:
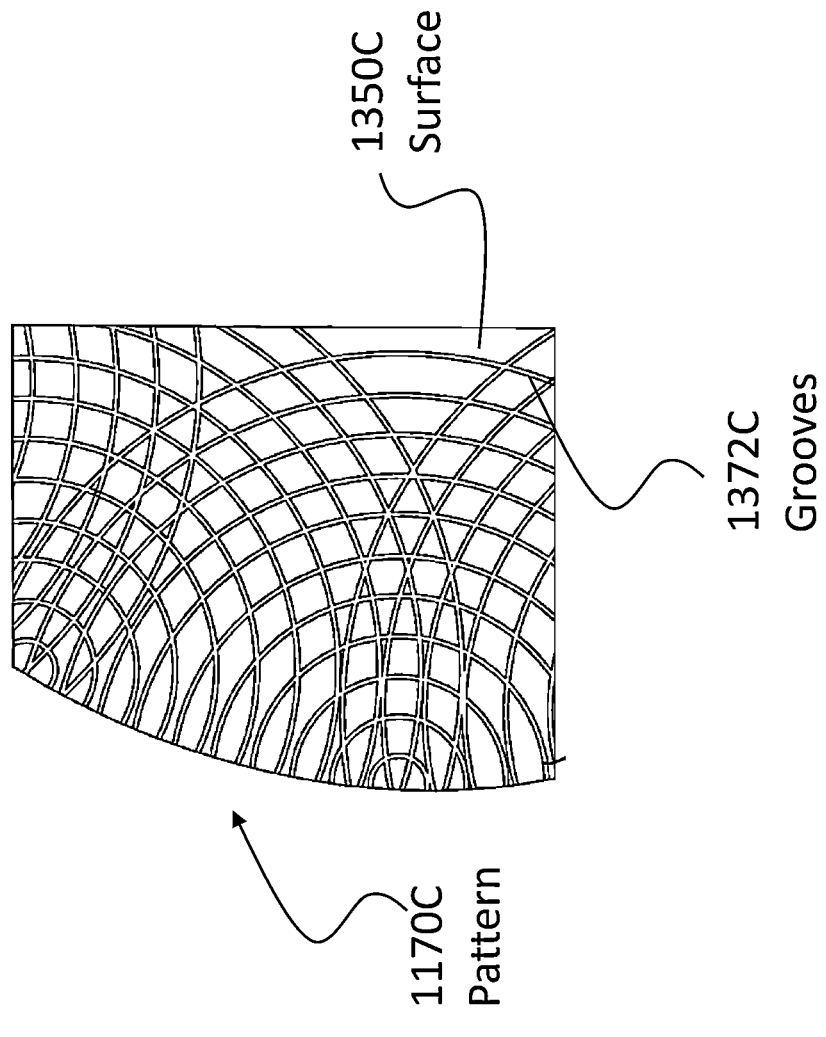

FIGS. 18A, 18B, and 18C illustrate further surface features that may be formed at locations on some exemplary implants. In this regard, in an exemplary embodiment, the surfaces can have surface discontinuity. For example, instead of and/or in addition to surface discontinuities achieved via the grooves detailed above, or the porous porous-solid scaffold of FIG. 17, some surfaces can include one or more of the surface features shown in FIGS. 18A-18C, which, in some embodiments, are patterned microstructures that are configured to promote osseointegration of an implantable component with a recipient's skull bone. (Note that as with the grooves, other portions of the pedestal 610 can include these surface features.)

FIG. 18A illustrates an arrangement in which a plurality of rounded or dome-shaped protrusions 1370A extend from a surface 1350A of the pedestal. It is noted that in some embodiments, the protrusions shown in FIG. 18A can be used in combination with a porous scaffold as described above. In certain such embodiments, a surface may include both osteoconductive pores and protrusions as describe above with reference to FIG. 18A.

FIGS. 18B and 18C illustrate further embodiments in which the surface features comprise a pattern of grooves disposed in a surface of the pedestal. More specifically, FIG. 18B illustrates a pattern 1370B of intersecting linear grooves 1372B (i.e., grooves formed as straight lines) in surface 1350B. FIG. 18C illustrates a pattern 1170C of intersection curved grooves 1372C (i.e., grooves formed as curved lines) in surface 1350C. The grooves 1372B and/or 1372C may have a depth in the range of approximately 50 micrometers to approximately 200 micrometers and a width in the range of approximately 70 micrometers to approximately 350 micrometers.

The shape of the grooves in the embodiments of FIGS. 18B and 18C the grooves are configured to promote bone growth in a direction that is substantially perpendicular to a surface of the recipient's skull.

As with the embodiment of FIG. 18A, the embodiments of FIGS. 18B and 18C can be in combination with a porous scaffold as described above. In certain such embodiments, the surfaces 1350B and 1350C may include both osteoconductive pores (as described above) and grooves as describe above. Again, in at least some embodiments, any one or more of the teachings detailed herein can be combined with any one or more other teachings detailed herein.

It is noted that the shapes of the grooves of FIGS. 18B and 18C can correspond to that of the grooves detailed above and/or variations thereof In some embodiments, the microstructure can be a plurality of elements 1372D in a crisscross pattern, overlapping one another (although in other embodiments, the elements do not overlap each other, or at least some of the elements do not overlap some of the other elements). In an exemplary embodiment, the elements 1372D correspond to grooves and/or the microstructures detailed herein and/or variations thereof. As can be seen, the elements 1372D would have a longitudinal axis that is offset from the longitudinal axis of the pedestal.

FIG. 13E depicts yet another alternate embodiment utilizing the exemplary grooves and/or microstructures detailed herein. More specifically, FIG. 13E a plurality of elements 1372E spaced apart from one another, where the elements are located on the outer circumference of the pedestal and/or the bottom surface of the pedestal. In an exemplary embodiment, the elements 1372E correspond to grooves and/or the microstructures detailed herein and/or variations thereof. In this exemplary embodiment, the elements 1372F are in the form of splines.

Figure 18D:
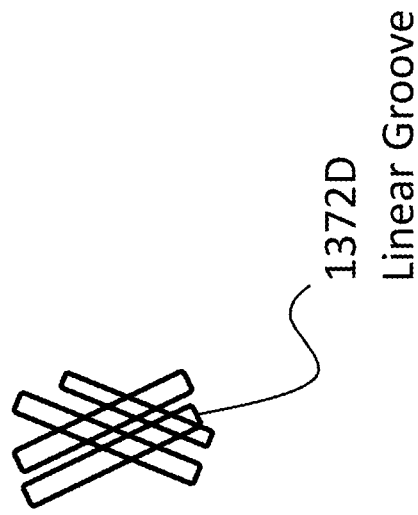
Figure 18E:
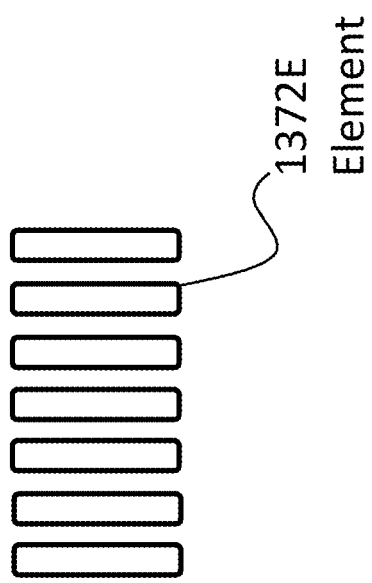
Figure 18F:
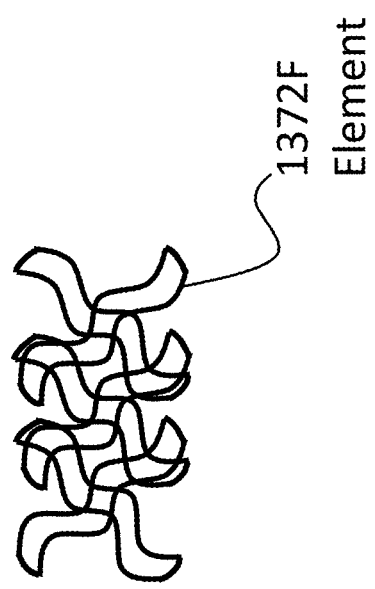

FIG. 18F depicts yet another alternate embodiment utilizing the exemplary grooves and/or microstructures detailed herein. More specifically, FIG. 13F depicts a plurality of elements 1372F overlapping each other (although in other embodiments, the elements do not overlap each other, or at least some of the elements do not overlap some of the other elements), where the elements are located on the outer circumference of the pedestal. In an exemplary embodiment, the elements 1372F correspond to grooves and/or the microstructures detailed herein and/or variations thereof. In the exemplary embodiment, the elements 1372F are in a wave form. In an exemplary embodiment, the wave form can be a predictable wave form (e.g., a sine wave) and/or can be in a chaotic wave form.

The elements 1372D, 1372E, and 1372F are configured to promote bone growth in a direction that is substantially perpendicular to a surface of the recipient's skull.

It is noted that alternate embodiments can have different geometries than those detailed in FIGS. 18D-18F. Also, embodiments of these FIGs. can be combined in some embodiments. As with all of the embodiments herein (unless stated otherwise), the elements of FIGS. 18D, 18E and/or 18F and the variations thereof can be applied at various locations.

Figure 18G:
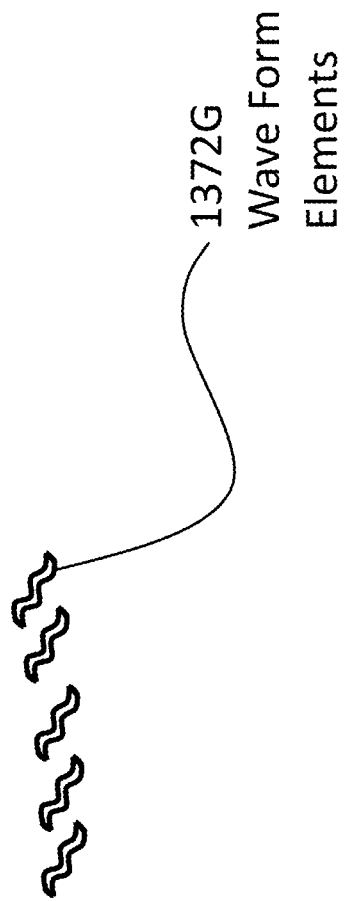
Figure 18H:
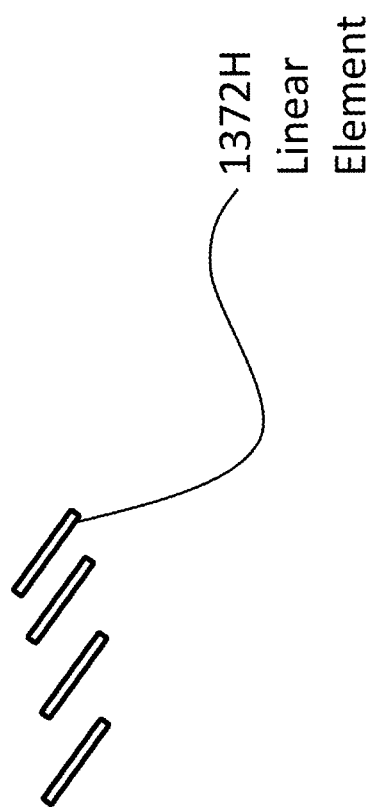
Figure 18I:
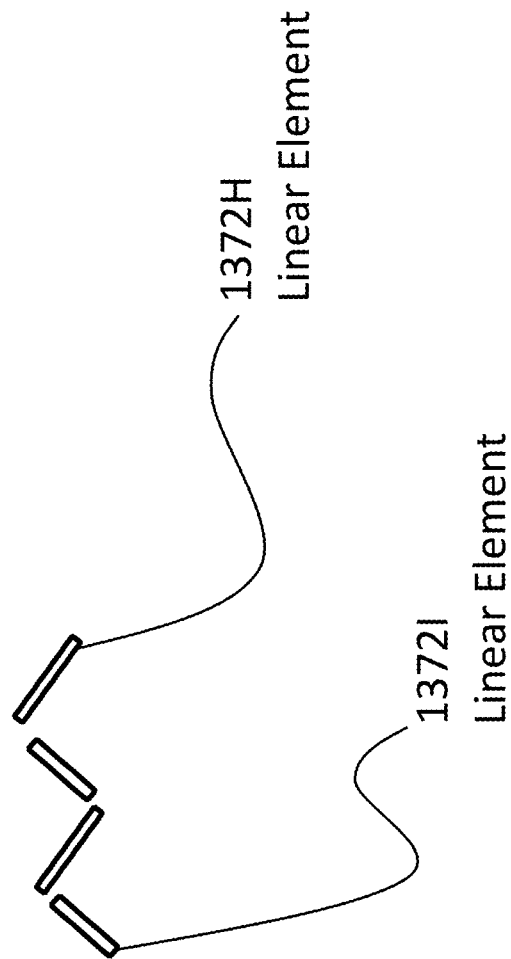
Figure 18J:
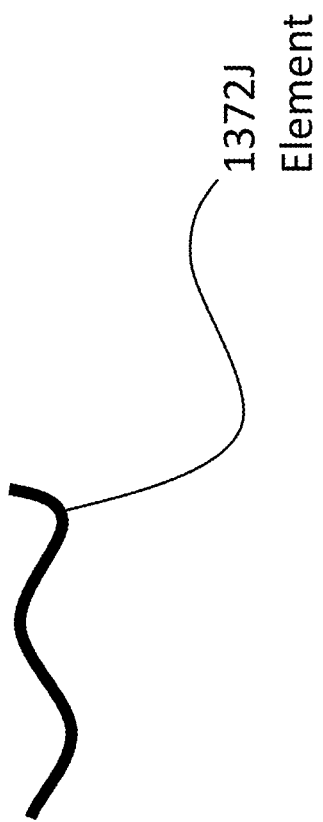

In this regard. FIG. 18G depicts an exemplary wave form elements 1372G. FIG. 18H depicts an alternate embodiment having linear elements 1372H arrayed on the face of the pedestal. As noted above, the linear elements 1372H can have a longitudinal axis lying on the plane that extends through and is parallel to the longitudinal axis of the pedestal (e.g., the elements can be arranged in a spline form). FIG. 18I depicts an alternate embodiment having linear elements 1372H and 1372I, except that the elements are located at different angles relative to one another. In some embodiments (as with all embodiments unless otherwise indicated, the elements can overlap one another). FIG. 18J depicts an alternate embodiment having an element 1372J that is in a wave form as it extends about the pedestal.

Figure 18K:
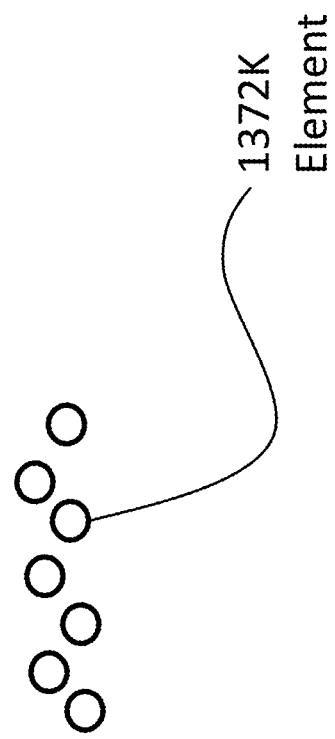

FIG. 18K depicts an alternate embodiment having elements 1372K. On an exemplary embodiment, the elements 1372K are hemispherical indentations in the surface, where the outer diameter is about 50 to about 200 nanometers, and the depth is about 70 to about 250 nanometers. Alternatively, these elements can be bumps having similar but opposite dimensions.

The elements of the FIGS. 13A-13K can correspond to the grooves and/or microstructures detailed herein and/or variations thereof. It is further noted that while the elements are detailed only on one face of the thread, in alternate embodiments, the elements can be located on both faces.

It is further noted that the elements of FIGS. 13A-13K and/or the grooves and/or microstructures detailed herein and/or variations thereof can have a width that varies. That is, for example, in the case of a groove, the width of the groove can widen and narrow along the longitudinal axis thereof.

In at least some exemplary embodiments, the pedestal is a monolithic structure made of commercially pure titanium or titanium-alloy. This includes at least some embodiments having the scaffold structure detailed above and/or the micro surface structure detailed above. That is, the monolithic structure of the pedestal 610 includes the scaffolds and/or microstructure noted above.

In an exemplary embodiment, surface roughness of at least some components of the pedestal 610, such as by way of example only and not by way of limitation, can be a relatively smooth machine surface with a typical roughness value $R_a$ (arithmetic roughness) between about 0.3 to about 0.9 μm ($S_a$=0.3 to 0.9 micrometers) or any value or range of values therebetween in about 0.01 μm increments. Alternatively, and/or in addition to this, some surfaces can be a medium rough surface obtained by for example, grit blasting acid etching, electromechanical working, and/or laser modification, etc.). In some exemplary embodiments, these medium rough surfaces can have a roughness value $R_a$ between about 0.9 μm to about 2.0 μm or any value or range of values therebetween in about 0.01 μm increments. Alternatively, and/or in addition to this, some surfaces can be a rough surface which can have a $R_a$ value between about 2.0 to 25 μm, or any value or range of values therebetween in about 0.01 μm increments. In an exemplary embodiment, such rough surfaces can be obtained by, for example, grit blasting, plasma-spraying or acid etching, and/or a three-dimensional trabecular mesh established thereon by, for example, additive manufacturing, etc. Still further, in an exemplary embodiment, some or all surfaces are treated with hydroxyapatite or an equivalent coating having a thickness from about 5 nm to about 40 μm or any value or range of values therebetween. In some embodiments, any surface, such as a modified surface, that promotes osseointegration, and/or enables faster and stronger bone formation, better stability during the healing process, and/or improved clinical performance in poor bone quality and quantity, relative to that which would be the case in the absence of such surface, can be utilized in at least some embodiments.

It is again reiterated that in at least some embodiments, any one or more of the teachings detailed herein can be combined with any other one or more teachings detailed herein. Conversely, any one or more of the teachings detailed herein can be explicitly excluded from use with any one or more of the other teachings detailed herein. Thus, some embodiments include embodiments that specifically do not have one or more of the teachings and/or features detailed herein.

Any disclosure herein of a device and/or a system corresponds to a disclosure of a method of making that device and/or system. Conversely, any disclosure herein of a method action of making the device and/or system corresponds to a resulting device and/or system made by that method action. Any disclosure herein of a method action corresponds to a disclosure of a device and/or system for executing that method action. Any disclosure herein of a device and/or system corresponds to a disclosure of utilizing that device and/or system. Any disclosure herein of a functionality of any apparatus corresponds to a method action of executing that functionality.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. An apparatus, comprising:
an implantable portion of a transcutaneous bone conduction device; and
a pedestal attached to the implantable portion, the pedestal configured to be implanted into a skull bone of a recipient.

2. The apparatus of claim 1, wherein:
the pedestal is threadless over at least a majority of a bone facing surfaces extending in the longitudinal direction of the pedestal.

3. The apparatus of claim 1, wherein:
the pedestal is releasably connected to the implantable portion.

4. The apparatus of claim 1, wherein:
the pedestal has a nonsmooth cylindrical face that interfaces with a skull bone.

5. The apparatus of claim 1, wherein:
the pedestal is configured to enable removal of the implantable portion from the pedestal without removing the pedestal from a skull.

6. The apparatus of claim 1, wherein:
the pedestal is a monolithic component that is at least one of rotationally symmetrical or rotationally symmetrical with the exception of pockets extending in a longitudinal direction.

7. The apparatus of claim 1, wherein:
the pedestal has a width that is larger than a height; and wherein the pedestal is made of metal.

8. The apparatus of claim 1, wherein:
the pedestal is a separate component from the implantable portion, and an interface between the pedestal and the implantable portion is self-sealed due to the attachment between the pedestal and the implantable portion.

9. The apparatus of claim 1, wherein:
the pedestal includes at least one pocket extending from a distal end towards the proximal end, the pocket being configured for at least one of bone anchoring, rotational stability or tool gripping for attachment of the pedestal to the implantable portion.

10. The apparatus of claim 1, wherein:
an average diameter measured normal to a longitudinal axis of the pedestal is greater than a maximum distance of extension in the longitudinal direction.

11. A method, comprising:
obtaining an implantable portion of a transcutaneous bone conduction device; and
attaching a pedestal to the implantable portion temporally proximate to implanting such into a recipient, the pedestal configured to be implanted into a skull bone of a recipient.

12. The method of claim 11, further comprising:
prior to the action of attaching the pedestal, choosing between the pedestal and a screw bone fixture available to a person attaching the pedestal at at least one of the time of choosing or the time of attaching.

13. The method of claim 11, further comprising:
obtaining a packaging in which the pedestal was stored and is supported thereby at the time of obtaining;
using the packaging to at least one of apply a torque or a countertorque to the pedestal during the action of attaching.

14. The method of claim 11, further comprising:
drilling a hole into a skull using a high-speed drill; and
placing the pedestal into the hole established at least in part by the action of drilling during an implantation process so as to implant the pedestal and the implantable portion into a head of the skull.

15. The method of claim 14, further comprising:
reaming the drilled hole prior to placing the pedestal into the hole established at least in part by the action of drilling.

16. The method of claim 15, wherein:
the actions of attaching, drilling, placing, and reaming are executed at least 50 times in association with different recipients of respective pedestals and implantable portions.

17. The method of claim 11, further comprising:
implanting the assembly of the pedestal and the implantable portion in a skull of a human, wherein the action of attaching is executed in temporal proximity to the action of implanting.

18. The method of claim 11, wherein:
an average diameter measured normal to a longitudinal axis of the pedestal is greater than a maximum distance of extension in the longitudinal direction.

19. An apparatus, comprising:
an osseointegrating lateral stability device configured for removable attachment to an implantable prosthetic component, the device having non-threaded bone interfacing surfaces extending for at least about half a longitudinal distance of the device.

20. The apparatus of claim 19, wherein:
the device is substantially rectangular in cross-section with the major exception of a central core component configured to receive an attachment component of the prosthetic component.

21. The apparatus of claim 19, wherein:
the device is no more than about 8 mm in diameter about a longitudinal axis and 4 mm high in a direction of the longitudinal axis.

22. The apparatus of claim 19, wherein:
the device is configured to osseointegrate into bone such that about a two Newton force applied in a longitudinal direction will displace the device from bone.

23. A kit, comprising:
the apparatus of claim 19; and
a storage component in which is received at least partially the apparatus, wherein
the storage component is configured in a form of a hand torque acting and/or reacting device configured to apply and/or prevent a rotation of the apparatus upon the screwing of a component into the apparatus.

24. The kit of claim 23, further comprising:
a sizing gauge configured to size a hole in a skull for confirmation that the hole size is suitable for the device.

* * * * *